US009046757B2

(12) United States Patent
Kang

(10) Patent No.: US 9,046,757 B2
(45) Date of Patent: Jun. 2, 2015

(54) MOVING IMAGE PICKUP APPARATUS, METHOD FOR OBSERVING MOVING IMAGE, MOVING IMAGE OBSERVING PROGRAM, AND COMPUTER-READABLE RECORDING MEDIUM

(75) Inventor: Woobum Kang, Osaka (JP)

(73) Assignee: Keyence Corporation, Osaka (JP)

(*) Notice: Subject to any disclaimer, the term of this patent is extended or adjusted under 35 U.S.C. 154(b) by 713 days.

(21) Appl. No.: 13/267,274

(22) Filed: Oct. 6, 2011

(65) Prior Publication Data
US 2012/0105664 A1 May 3, 2012

(30) Foreign Application Priority Data

Oct. 29, 2010 (JP) ................................. 2010-244723
Oct. 29, 2010 (JP) ................................. 2010-244724
Oct. 29, 2010 (JP) ................................. 2010-244725

(51) Int. Cl.
*H04N 5/225* (2006.01)
*G03B 39/00* (2006.01)
*G01N 21/88* (2006.01)
*G06K 9/00* (2006.01)
*G06K 9/62* (2006.01)
*H04N 5/345* (2011.01)

(52) U.S. Cl.
CPC ............ G03B 39/00 (2013.01); G01N 21/8851 (2013.01); *G01N 2021/889* (2013.01); *H04N 5/3454* (2013.01); G06K 9/00718 (2013.01); G06K 9/6284 (2013.01)

(58) Field of Classification Search
USPC ........................................... 348/207.99–376
See application file for complete search history.

(56) References Cited

U.S. PATENT DOCUMENTS

| 2005/0075537 A1* | 4/2005 | Chen et al. ..................... 600/109 |
| 2007/0230893 A1* | 10/2007 | Meron et al. ...................... 386/4 |
| 2009/0002485 A1 | 1/2009 | Fujiwara |
| 2009/0102938 A1 | 4/2009 | Takahashi et al. |
| 2009/0189994 A1 | 7/2009 | Shimonaka |
| 2010/0053319 A1* | 3/2010 | Sakai et al. ................... 348/125 |

FOREIGN PATENT DOCUMENTS

| JP | 2007-243846 A | 9/2007 |
| JP | 2008-242812 A | 10/2008 |
| JP | 2009-008918 | 1/2009 |
| JP | 2009-017481 | 1/2009 |
| JP | 2009-100326 | 5/2009 |
| JP | 2009-141709 | 6/2009 |
| JP | 2009-141710 | 6/2009 |
| JP | 2009-177537 | 8/2009 |

* cited by examiner

*Primary Examiner* — Anthony J Daniels
(74) *Attorney, Agent, or Firm* — Kilyk & Bowersox, P.L.L.C.

(57) ABSTRACT

A moving image is divided with imaging timing aligned without using a synchronous input. A moving image pickup apparatus to pick up a moving image of one or more objects as an imaging target includes an image obtaining unit for obtaining an input moving image composed of a plurality of frames containing a scene of the object making a periodic motion, a representative image selecting unit for selecting a representative image representing a cycle, a standard timing selecting unit for selecting a standard timing based on the representative image, in order to divide the input moving image obtained by the image obtaining unit with respect to each cycle, and a cycle extracting unit for dividing the input moving image with respect to each cycle, based on the standard timing selected by the standard timing selecting unit.

18 Claims, 20 Drawing Sheets

MOVING IMAGE PICKUP APPARATUS, METHOD FOR OBSERVING MOVING IMAGE, MOVING IMAGE OBSERVING PROGRAM, AND COMPUTER-READABLE RECORDING MEDIUM

CROSS-REFERENCE TO RELATED APPLICATIONS

The present application claims foreign priority based on Japanese Patent Application No. 2010-244723, filed Oct. 29, 2010, No. 2010-244724, filed Oct. 29, 2010, and No. 2010-244725, filed Oct. 29, 2010, the contents of which is incorporated herein by reference.

BACKGROUND OF THE INVENTION (1) Field of the Invention

The present invention relates to a moving image pickup apparatus which can pick up an image at a high frame rate such as a high-speed imaging camera, a method for observing a moving image, a moving image observing program, and a computer-readable recording medium.

(2) Description of the Related Art

In order to photograph a change of an object, a high-speed imaging camera is used to serially pick up an image at a high frame rate. This apparatus displays frame image data picked up by an imaging unit at a predetermined imaging frame rate, on a display unit at a frame rate different from that at the time of imaging. For example, while an imaging cycle for an image is 1/30 second, that is, a frame rate is a standard speed of 30 fps (frame per second) in a usual video camera, a high frame rate such as 60 to 32000 fps can be set in the high-speed camera. When a moving image is recorded with the above high-speed camera, and a series of frame image data picked up at the high imaging frame rate is displayed on a display screen at a frame rate lower than that at the time of imaging, the series of image data of the motion of the object picked up with respect to each fine time can be observed in slow motion (refer to Japanese Unexamined Patent Publication Nos. 2009-141709 and 2009-100326).

Regarding the moving image picked up by the high-speed imaging apparatus, as the imaging frame rate increases, a playback time becomes extremely long compared to the imaging time, so that it is difficult to find out a desired picked-up image from enormous frame image data. Especially, as the high-speed camera is increased in speed, and the frame rate becomes high, that is, as the number of picked-up images per unit time increases, a moving image data amount to be analyzed becomes enormous, and the problem becomes more serious.

In addition, it is not easy to analyze an imaging target object contained in the image. For example, in a case where a product moving on a production line is serially photographed by the high-speed imaging apparatus to discover a cause of certain abnormality, when the time when abnormality is generated can be specified to some extent, it is only necessary to analyze an image around that time, but when the time is not known, the moving image has to be serially picked up for a long time, and a user has to visually confirm these images, so that the user has to visually confirm the images one by one so as to find out an abnormality generation process from the enormous image data containing the similar image, which forces the user to bear an extremely hard workload. At this time, when there is a certain index to make an analysis and the analysis is made based on the index, the workload can be considerably lightened.

Meanwhile, conventionally, by synchronizing an imaging operation with an input of another signal, that is, a synchronization signal such as a trigger signal to detect the generation of the abnormality, the moving image data is analyzed in the vicinity of the input timing of the trigger signal. However, according to this method, an additional sensor is needed to externally input the synchronization signal, and system architecture is needed to record the moving image by being linked with the synchronization signal. In addition, when the synchronization signal cannot be obtained, or a method to obtain it is not known, the above method cannot be used. Therefore, a simple method capable of obtaining an index of analysis with only the obtained image data has been needed.

SUMMARY OF THE INVENTION

The present invention was made in view of the conventional problems. It is a main object of the present invention to provide a moving image pickup apparatus, a method for observing a moving image, a moving image observing program, and a computer-readable recording medium capable of providing an analysis index to a user in analyzing picked-up moving image data.

In order to attain the above object, according to one embodiment of a moving image pickup apparatus in the present invention, the moving image pickup apparatus to pick up a moving image of one or more objects as an imaging target includes an image obtaining unit for obtaining an input moving image composed of a plurality of frames containing a scene of the object making a periodic motion, a representative image selecting unit for selecting a representative image representing a cycle, a standard timing selecting unit 31 for selecting a standard timing based on the representative image, in order to divide the input moving image obtained by the image obtaining unit with respect to each cycle, and a cycle extracting unit 32 for dividing the input moving image with respect to each cycle, based on the standard timing selected by the standard timing selecting unit 31. Thus, since the obtained input moving image can be periodically divided, an analyzing operation of the moving image by the user can be considerably reduced, and in analyzing the moving image containing a great amount of image frames with a high-speed camera especially, the analysis can be effectively made.

In addition, according to another embodiment of the moving image pickup apparatus, the representative image selecting unit can be configured to automatically select the representative image. Thus, since the input moving image can be periodically divided using the automatically selected representative image as an image trigger, the analyzing operation of the moving image by the user can be considerably reduced.

In addition, according to still another embodiment of the moving image pickup apparatus, the representative image selecting unit can be configured to select an image surely appearing one time in each cycle, as the representative image.

In addition, according to yet another embodiment of the moving image pickup apparatus, the representative image selecting unit can be configured to make a user select the representative image.

In addition, according to yet another embodiment of the moving image pickup apparatus, it may further include a cycle adjusting unit 33 for adjusting a position of the cycle backward and forward before the input moving image is divided with respect to each cycle by the cycle extracting unit 32. Thus, the user can finely adjust the cycle before the moving image is divided with respect to each cycle.

In addition, according to yet another embodiment of the moving image pickup apparatus, it may further include a phase adjusting unit for calculating a difference by shifting the frame of the divided moving images as a target when the phases of the divided moving images are not known, and regarding a position having a highest evaluation value as a position having an aligned phase. Thus, even when the phase of the moving image is not known, the position in which the phase is aligned can be appropriately obtained by the calculation.

In addition, according to yet another embodiment of the moving image pickup apparatus, it may further include a characteristic amount calculating unit 34 for calculating a characteristic amount of each frame or each frame group from the input moving image obtained by the image obtaining unit, based on the representative image, and a moving picture waveform generating unit 35 for generating a moving picture waveform, based on the characteristic amount calculated by the characteristic amount calculating unit 34, in which the standard timing selecting unit 31 can select the standard timing, based on the moving picture waveform. Thus, a quantitative evaluation can be made based on the moving picture waveform, and the division can be easily made with respect to each cycle using the moving picture waveform.

In addition, according to yet another embodiment of the moving image pickup apparatus, the standard timing selecting unit 31 can regard a time when the picture waveform exceeds a predetermined threshold value as the standard timing. Thus, each cycle can be synchronized by the standard timing, so that the periodic division can be made without a synchronous input.

In addition, according to yet another embodiment of the moving image pickup apparatus, the standard timing selecting unit 31 can regard a time when the characteristic amount of the moving picture waveform reaches a maximum amount or a minimum amount in a predetermined period as the standard timing.

In addition, according to yet another embodiment of the moving image pickup apparatus, it may further include a trigger outputting unit for outputting a trigger signal at a time corresponding to the standard timing.

In addition, according to yet another embodiment of the moving image pickup apparatus, it may further include an abnormality degree analyzing unit 38 for determining an abnormality degree by comparing a previously determined standard motion pattern for the one cycle representing a standard motion of the object, with the input moving image in each cycle, a primary memorizing unit 53 for storing the moving image data obtained by the image obtaining unit with respect to each cycle, and a stored image extracting unit 36 for specifying the moving image in the cycle having a high abnormality degree determined by the abnormality degree analyzing unit 38 to be stored in the primary memorizing unit 53. Thus, only the moving image having the high abnormality degree can be left in the primary memorizing unit.

In addition, according to yet another embodiment of the moving image pickup apparatus, it may further include a secondary memorizing unit 56 having large memory capacity and low in writing speed as compared to the primary memorizing unit 53, in which among the imaging data stored with respect to each cycle in the primary memorizing unit 53, the moving image in the cycle determined to be left in the secondary memorizing unit 56 because of the high abnormality degree by the stored image extracting unit 36 can be stored in the secondary memorizing unit 56. Thus, the moving image in the cycle having the higher importance degree can be surely stored in the secondary memorizing unit.

In addition, according to yet another embodiment of the moving image pickup apparatus, the characteristic amount calculating unit 34 includes the abnormality degree analyzing unit 38, and the abnormality degree can be used as the characteristic amount. Thus, the input moving image is divided with respect to each cycle using the characteristic amount, while the characteristic amount can be used as the abnormality degree in selecting the moving image to be stored.

In addition, according to yet another embodiment of the moving image pickup apparatus, it may further include a displaying unit 52 for displaying the input moving image, in which the displaying unit 52 includes an image display region 41 for displaying the moving image, and a waveform display region 42 for displaying the moving picture waveform generated by the moving picture waveform generating unit 35, and when an arbitrary position of the moving picture waveform is selected in the waveform display region 42, the moving image corresponding to the selected moving picture waveform can be displayed in the image display region 41. Thus, the moving image is linked with the moving picture waveform, and the position of the image frame of the corresponding moving image can be designated from the moving picture waveform, so that the moving picture waveform can be used as an index of the moving image.

In addition, according to yet another embodiment of the moving image pickup apparatus, the standard timing can be changed by the standard timing selecting unit 31 under the condition that the moving picture waveform showing the characteristic amount is displayed in the waveform display region 42, and when the standard timing is changed, the moving picture waveform displayed in the waveform display region 42 can be accordingly updated. Thus, the user can adjust or change the timing to the appropriate standard timing while referring to the moving picture waveform after changed.

In addition, according to yet another embodiment of the moving image pickup apparatus, the representative image can be changed under the condition that the moving picture waveform showing the characteristic amount is displayed in the waveform display region 42, and when the representative image is changed, the moving picture waveform displayed in the waveform display region 42 can be accordingly updated. Thus, the user can select the appropriate representative image while referring to the moving picture waveform after changed.

In addition, according to yet another embodiment of the moving image pickup apparatus, the image obtaining unit is an imaging unit 10 capable of picking up the input moving image of the object at an imaging cycle of not more than ½₅ second. Thus, the analysis can be effectively made in analyzing the moving image containing the great amount of image frames.

In addition, according to one embodiment of a method for observing a moving image of one or more objects as an imaging target, it includes the steps of obtaining an input moving image composed of a plurality of frames containing a scene of the object making a periodic motion, calculating a characteristic amount of each frame or each frame group from the obtained input moving image by a characteristic amount calculating unit 34, generating a moving picture waveform, based on the calculated characteristic amount, obtaining a standard timing to determine a cycle of the moving picture waveform by a standard timing selecting unit 31, based on the moving picture waveform, and dividing the input moving image with respect to each cycle, based on the standard timing. Thus, each cycle can be synchronized by the standard timing, and the division can be made with respect to each cycle without the synchronous input. In addition, the quantitative evaluation can be made based on the moving picture waveform, and the division can be easily made with respect to each cycle using the moving picture waveform.

In addition, according to one embodiment of a moving image observing program to observe a moving image of one or more objects as an imaging target, it causes a computer to implement the functions of obtaining an input moving image composed of a plurality of frames containing a scene of the object making a periodic motion, calculating a characteristic amount of each frame or each frame group from the obtained input moving image, generating a moving picture waveform, based on the calculated characteristic amount, selecting a standard timing to determine a cycle of the moving picture waveform by comparing the moving picture waveform with a predetermined threshold value, and dividing the input moving image with respect to each cycle, based on the selected standard timing to be executed in a computer. Thus, each cycle can be synchronized by the standard timing, and the division can be made with respect to each cycle without the synchronous input. In addition, the quantitative evaluation can be made based on the moving picture waveform, and the division can be easily made with respect to each cycle using the moving picture waveform.

In addition, according to one embodiment of a computer-readable recording medium, it stores the above-described program. The recording medium includes a medium capable of storing a program, such as a magnetic disk, an optical disk, a magneto optical disk, or a semiconductor memory. For example, it includes a CD-ROM, CD-R, CD-RW, flexible disk, magnetic tape, MO, DVD-ROM, DVD-RAM, DVD-R, DVD+R, DVD-RW, DVD+RW, Blu-ray, HD, and DVD (AOD). In addition, the program includes a program distributed by downloading through a network line such as the Internet as well as a program stored in the recording medium and distributed. In addition, the recording medium includes a program-recordable device such as a general-purpose or dedicated device in which the above program is installed so as to be executed in the form of software or firmware. Furthermore, each process and function contained in the program may be executed by computer-executable program software, or a process in each section may be implemented in the form of hardware such as a predetermined gate array (FPGA or ASIC), or in the form composed of program software and partial hardware module serving as a partial component of the hardware.

DETAILED DESCRIPTION OF PREFERRED EMBODIMENTS

Figure 1:
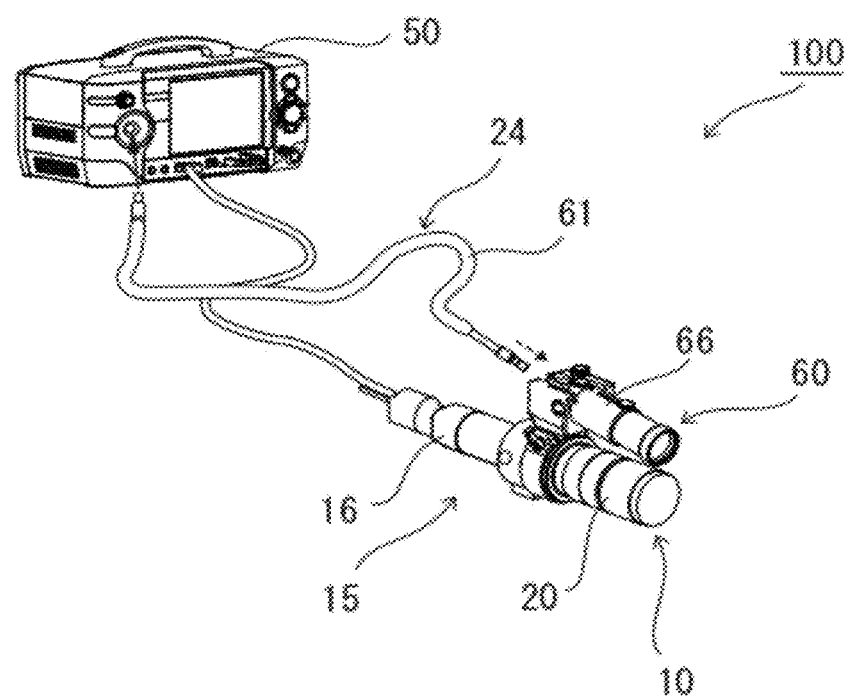
FIG. 1 is a perspective outline view showing a moving image pickup apparatus according to one embodiment of the present invention.

Hereinafter, an embodiment of the present invention will be described with reference to the drawings. Here, it is to be noted that the embodiment shown below only illustrates a moving image pickup apparatus, a method for observing a moving image, a moving image observing program, and a computer-readable recording medium to embody a technological thought of the present invention, and the present invention is not limited to the following moving image pickup apparatus, method for observing the moving image, moving image observing program, and computer-readable recording medium. In addition, this specification does not specify a member shown in the claims to a member in the embodiment. Especially, a dimension, material, shape, its relative arrangement, and the like of a component disclosed in the embodiment do not limit a range of the present invention only to themselves, and they are just an example unless otherwise noted. In addition, a size of the member, its positional relationship, and the like shown in each drawing are sometimes exaggerated to clarify the description. Moreover, the same name and reference symbol are allocated to the same or equivalent member, and its detailed description is accordingly omitted in the following description. Furthermore, each component of the present invention may be realized in such a manner that the plurality of components constitute one member and the plurality of components are shared by the one member, or a function of the one member is shared by the plurality of members. In addition, the contents described in a part of a working example and the embodiment may be used in another working example and embodiment.

The moving image pickup apparatus used in the working example of the present invention is electrically, magnetically, or optically connected to a peripheral device such as a computer, a printer, or an external memory apparatus through a serial connection such as IEEE1394, RS-232x, RS-422, or USB, a parallel connection, or the network such as 10BASE-T, 100BASE-TX, or 1000BASE-T to communicate with each other for a process such as an operation, control, or display. The connection is not limited to a physical connection using a cable and it may be a wireless connection using a wireless LAN such as IEEE802.1x, a radio wave such as Bluetooth (registered trademark), an infrared ray, or optical communication. In addition, the recording medium to exchange data, or to store the settings may be a memory such as a memory card, a magnetic disk, an optical disk, a magneto optical disk, or a semiconductor memory. In addition, the moving image pickup apparatus in this specification includes not only the moving image pickup apparatus itself but also a moving image pickup system in which the above apparatus is combined with the peripheral device such as the computer, or the external memory device.

In addition, the moving image pickup apparatus in this specification is not limited to a system itself to pick up an image with high-speed observation, or an apparatus or a method to perform a process such as an input/output, display, calculation, or communication related to the imaging operation, in a hardware manner. An apparatus or a method to perform a process in a software manner is also included in the range of the present invention. That is, the moving image pickup apparatus in the present invention includes an apparatus or a system which can pick up an image or perform a process related to the imaging operation by combining a general-purpose circuit or computer with software, program, plug-in, object, library, applet, compiler, module, or macro which is operated on a specific program. In addition, the computer in this specification includes a general-purpose or dedicated electronic computer and an electronic device such as a work station, terminal, portable electronic device, PDC, CDMA, W-CDMA, FOMA (registered trademark), GSM, IMT2000, fourth generation mobile phone, PHS, PDA, pager, or smartphone. In addition, the program in this specification is not limited to a program used alone, and it may be used as a support program such as functioning as a part of a specific computer program, software, or service, functioning as a program called when needed, being provided as a service in an environment such as the OS, operating as a resident program in the environment, or operating in a background.

The high-speed observation in this specification is also called high-speed imaging, which means that an instantaneous image which is difficult to see with human eyes is picked up as a plurality of continuous frame images, and for example, the image is picked up at a frame rate (defined by the number of the images continuously taken for one second) of 100 fps to a million fps. In this case, an object can optionally be displayed in an enlarged manner when needed.

In addition, the high-speed imaging means that still images are continuously picked up in general, but here, it is occasionally called a recording of a moving image for convenience sake because when the still images are continuously displayed, they can be handled as the moving image. That is, the moving image in this specification means a series of still images continuously picked up at a predetermined frame rate. In addition, a screen on which the moving image is displayed by a displaying unit 52 is called an image frame or image data.

Figure 2:
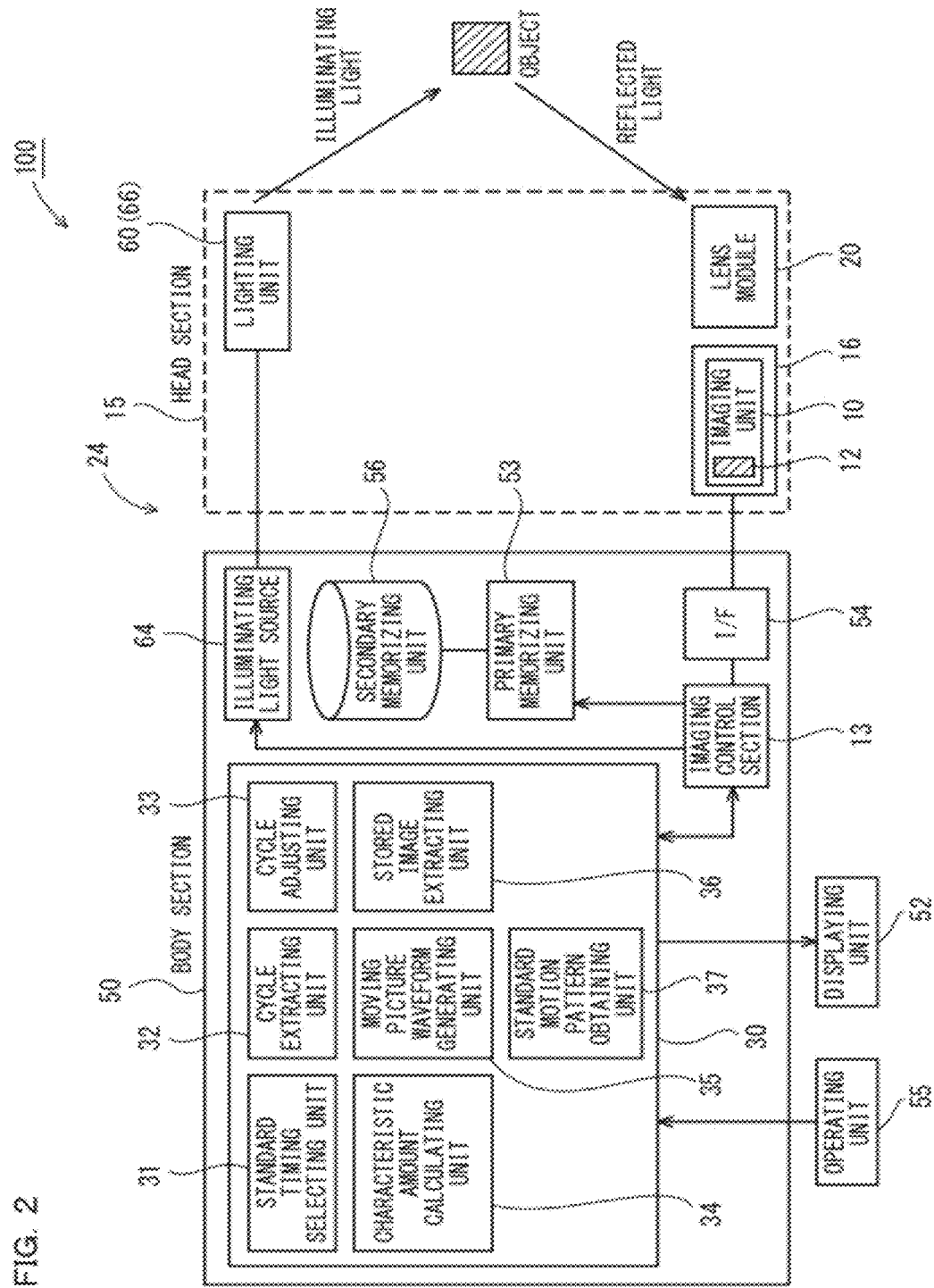
FIG. 2 is a block diagram of the moving image pickup apparatus shown in FIG. 1.

FIG. 1 is a perspective outline view of a moving image pickup apparatus 100 according to one embodiment of the present invention, and FIG. 2 is a block diagram thereof. The moving image pickup apparatus 100 shown in the drawings includes a head section 15 having an imaging unit 10 serving an image obtaining unit, a body section 50 to drive and control the head section 15 to perform an image processing, and a cable section 24 to connect them. The head section 15 includes an imaging module 16 including the imaging unit 10, a lighting module 66 including a lighting unit 60, and a lens module 20. The body section 50 includes an illuminating light source 64 to supply illuminating light to the lighting unit 60, an imaging control section 13 to generate a imaging control signal to control the imaging unit 10 and transmit it to the imaging unit 10, and an image processing section 30 to perform the image processing for a moving image picked up by the imaging unit 10. Furthermore, the body section 50 includes a displaying unit 52 for displaying the moving image picked up by the imaging unit 10, and an operating unit 55 through which a user performs various setting and operations. When the lens module 20 and the illuminating module 66 can be exchanged in the moving image pickup apparatus 100 according to observation purposes, the one moving image pickup apparatus can be used for various different purposes.

In addition, when needed, the body section 50 includes an imaging cycle setting unit for changing an imaging cycle of the imaging unit 10, a reading region determining unit for determining a size and/or a position of a reading region in which the image data can be read from an imaging region of the imaging unit 10 based on the imaging cycle, a display updating unit for detecting that the imaging cycle has been changed, reading the image frame from the reading region based on the size and/or the position of the reading region corresponding to the imaging cycle after changed, and displaying it on the displaying unit 52 at a predetermined display cycle, a region displaying unit 52 for displaying a region display showing the size and/or the position of the reading region on the displaying unit 52, a region display adjusting unit for adjusting a standard position of the region display, a region position designating unit for designating the standard position and the size of the reading region, an update indicating unit through which the user indicates execution of updating of the display of the moving image, a shutter speed setting unit for setting a shutter speed, and a trigger setting unit for setting a trigger.

The moving image pickup apparatus 100 can display the series of image data picked up by the imaging unit 10 on the displaying unit 52 as the moving image at a display cycle slower than the imaging cycle at the time of imaging. That is, it can play back the picked-up moving image at slow speed.

(Head Section 15)

The Head Section 15 has the Imaging Unit 10 in the Imaging Module 16. The imaging unit 10 has an imaging element 12 which electrically reads reflected light coming from an object S (a sample or a work), through an optical system, as an observation target illuminated by the illuminating unit 60. As the imaging element 12, a CMOS is used in this example, but another imaging element such as a CCD can be also used. Here, as for an outline of the head section 15, the imaging module 16 has a cylindrical shape as shown in FIG. 1, and incorporates the imaging element 12. In addition, by preparing various kinds of imaging modules 16 according to purposes such as black-and-white imaging or color imaging, and appropriately selecting them, the moving image pickup apparatus can be used for various kinds of purposes.

(Imaging Unit 10)

As for the imaging unit 10, the imaging element 12 is arranged in a two-dimensional manner and the image data picked up in at least one part of the imaging region of the imaging elements 12 can be read. That is, the image data from the whole imaging region of the imaging element is not always read, but the image data is picked up from the limited region based on the imaging cycle, so that high-speed reading can be performed. The imaging cycle (that is, an imaging frame rate which is occasionally called the "frame rate" simply in this specification unless otherwise stated) when the object is picked up by the imaging unit 10 can be changed to different cycles. The frame rate can be set within a range of 30 to 32000 fps.

In addition, the image obtaining unit is not limited to the imaging unit for taking the moving image, and it may obtain moving image data in such a manner that the moving image data which has been already picked up is inputted. The moving image data obtained by the image obtaining unit is composed of a plurality of frames including a scene of the object moving periodically. In addition, the image obtaining unit may be switched such that when abnormality is monitored or the image is inspected online, the image obtaining unit serves as the imaging unit for taking the moving image, and when abnormality is monitored or the image is inspected offline, it obtains the moving image data by inputting the moving image data which has been already picked up.

(Lens Module 20)

The lens module 20 incorporates an optical lens optically connected to the imaging element 12. The lens module 20 has a plurality of optical lenses having sizes and curvatures which are appropriate to required magnification and brightness. In addition, other than the lens module incorporating the lens for the high-speed observation, a lens module incorporating a lens for zoom observation may be prepared and replaced with the above lens module.

(Illuminating Unit 60)

The illuminating unit 60 illuminates the object S which is to be taken by the imaging element 12 through the lens module image 20. The light source of the illuminating unit 60 is incorporated in the body section 50, and the illuminating light is transmitted to the illuminating unit 60 of the head section 15 through the cable section 24. The illuminating unit 60 may be incorporated in the head section 15, or separately provided so as to be detachable from the head section 15.

(Body Section 50)

The body section 50 includes the illuminating light source 64, the imaging control section 13, the image processing section 30, a primary memorizing unit 53, and an interface section 54. According to the example in FIG. 2, each member is incorporated in the body section 50, but the body section 50 is not limited to the above configuration, and each of the illuminating light source 64, the imaging control section 13, the image processing section 30 can be split into units. Thus, a degree of freedom of the configuration increases. For example, the illuminating light source may not be incorporated and may be externally connected. In this case, the light source can be easily changed, but the light source needs to be arranged or wired, which is troublesome.

(Illuminating Light Source 64)

Lighting of the illuminating light source 64 is controlled by the imaging control section 13. More specifically, when a metal halide lamp or a halogen lamp is used, a mask plate (not shown) to mask all or part of the illuminating light to shield it is arranged on a light path of a connecting terminal to connect an illuminating light supply cable 61. The mask plate is configured such that two small and large substantially fan-shaped plates are connected with their backs to each other, and attached such that it can be turned around a turning axis. The large fan-shaped plate is provided with opening windows such as a substantially circle-shaped overall illuminating opening window and a substantially fan-shaped side illuminating opening window. In addition, the small fan-shaped plate has a gear groove in its circumferential side part. The mask plate is connected such that it can be turned around the turning axis and turned by a motor. As for the motor, a worm gear is fixed to a rotation axis, and a gear section of the worm gear is arranged so as to engage with the gear groove provided in an arc section of the small fan-shaped plate of the mask plate. When the mask plate is turned by rotating the motor, the overall illuminating opening window or the side illuminating opening window coincides with the illuminating light supply cable 61. Thus, the illuminating light supply cable 61 is connected to the illuminating light source 64, and the illuminating light can be emitted from the illuminating unit 60.

In addition, other than the metal halide lamp, a mercury lamp, a xenon lamp, a halogen lamp, or a LED may be used. As for the LED, an infrared component is small compared to the halogen lamp and the metal halide lamp, so that the merit is that a heat value to the object is small when the same light amount is applied. In addition, it is relatively inexpensive, has a long life, and superior in responsiveness to the input, so that the lighting can be controlled without using the mask plate to shield the illuminating light, and its ON/OFF can sufficiently follow the high-speed imaging such as one million fps.

(Imaging Control Section 13)

The imaging control section 13 sets an imaging condition such as the frame rate and the shutter speed at the time of high-speed observation through the operating unit 55, and controls each section based on the set imaging condition. More specifically, the imaging control section 13 generates an imaging control signal to drive and control the imaging element 12 of the imaging unit 10, and transmits it to the imaging unit 10. In addition, the imaging control section 13 controls ON/OFF and light shielding of the illuminating light source 64. For example, when the imaging is performed with strobe light, the imaging control section 13 outputs a synchronous signal which is synchronized with the imaging operation, turns ON/OFF the illuminating light source 64 by the synchronous signal, and performs the imaging operation with the imaging element 12. Thus, an imaging timing signal which is synchronized with start and end points of one imaging operation, and an exposure timing signal which is synchronized with an exposure start point of each frame during the imaging operation are transmitted from the imaging control section 13 to the illuminating light source 64.

(Image Processing Section 30)

The image processing section 30 performs the image processing to the image picked up by the imaging unit 10. For example, the image processing section 30 designates a region for the image of the object displayed on the displaying unit 52, and performs a measurement process to calculate an area or calculate a difference in height, a distance, and an angle thereof.

(Displaying Unit 52)

The displaying unit 52 displays the picked-up image and the settings. As the displaying unit 52, a CRT, a liquid crystal panel, or an organic EL is used. While the displaying unit 52 is incorporated in the body section 50 in the example in FIG. 1, a video image output terminal may be provided to connect an external display.

(Primary Memorizing Unit 53)

The primary memorizing unit 53 stores the picked-up image data and the setting contents. Preferably, a high-speed semiconductor memory such as a RAM is used as a temporal memory region, and a hard disk is used as a data storage region.

(Interface Section 54)

In addition, the interface section 54 is provided to exchange the data with an external device through an I/O or a communication line. As a port to exchange the control signal or the image data with the external device, a terminal hole to connect the cable section 24 and various connectors is opened in the body section 50. In addition, when a USB port is provided, the data can be easily written to a USB memory, or data can be easily exchanged with another computer through the serial connection.

(Operating Unit 55)

The operating unit 55 is an input/output device through which the user performs an operation such as inputting, based on the screen displayed on the displaying unit 52. The operating unit 55 is connected to the body section 50 via cable or radio, or fixed to the body section 50. The general operating unit 55 includes various kinds of pointing devices such as a mouse, keyboard, slide pad, track point, tablet, joystick, console, jog dial, digitizer, light pen, numerical keypad, touch pad, or accu point. In addition, the operating unit 55 can be used to operate the moving image pickup apparatus itself or its peripheral device as well as the operation to the moving image pickup apparatus. Furthermore, through a touch screen or a touch panel of the display which displays an interface screen, the user can perform the input or the operation by directly touch the screen by hand, or an existing inputting unit such as a voice input can be used, or they can be used together. In addition, the displaying unit 52 and the operating unit 55 can be integrally combined with the body section 50, or externally connected to the body section via cable or radio. Furthermore, when the displaying unit includes the touch panel, the displaying unit and the operating unit can be integrally constituted. In addition, the operating unit 55 may be composed of the console connected without cable.

(Function of Image Processing Section 30)

The image processing section 30 has a function to divide the moving image with respect to each cycle, to store the divided moving image having a high degree of abnormality among the divided moving images, and to compare and analyze the divided moving images. The image processing section 30 shown in FIG. 2 includes a characteristic amount calculating unit 34, a cycle extracting unit 32, a standard timing selecting unit 31, a moving picture waveform generating unit 35, a stored image extracting unit 36, and a standard motion pattern obtaining unit 37 (which will be described later).

(Moving Image Dividing Function)

The moving image pickup apparatus has the moving image dividing function to divide the moving image having a scene in which a similar motion is periodically made, with respect to each cycle. More specifically, a representative image which represents the cycle is selected, and a waveform showing a degree of similarity with the representative image is created as a moving picture waveform, and by analyzing the waveform, the moving image is divided with respect to each cycle with its phase aligned. In this way, the moving image containing many frames can be divided with respect to each cycle, and the comparison and analysis can be easily made based on the divided cycle. According to the moving image dividing function, the phase can be aligned when the divided moving images are compared. Thus, the moving images having the different cycles can be compared with the phases aligned, that is, pieces of image data having the same phase are compared with each other, so that the analysis operation can be conveniently performed. The moving image dividing function can be implemented with the standard timing selecting unit 31 and the cycle extracting unit 32.

(Representative Image)

Here, the representative image is used when a reference value of each frame is calculated and the moving picture waveform is calculated, and this image is appropriately used to divide the cycle. Since a division point of the cycle is determined based on the representative image, the representative image is preferably selected as the image which can surely appear in each cycle and represents the cycle. Furthermore, a threshold vale regarding the reference value is set for the moving picture waveform formed based on the representative image, and the image is preferably selected as the representative image such that a time when the moving picture waveform exceeds the threshold value or a time when it falls below the threshold value can be set to its standard timing. In addition, similar to the case where the standard timing is searched with the threshold value, the image is preferably selected as the representative image such that the standard timing can be searched by a simple method such as a method in which the standard timing is searched by searching a minimum or maximum value in the moving picture waveform provided based on the representative image in a certain time zone.

This representative image can be automatically calculated as well as being arbitrarily selected from the picked-up moving image by the user. In the above method, the representative image is automatically calculated once with the image observing program and adjusted by the user. In an example in FIG. 9, the representative image automatically selected by the standard timing selecting unit 31 is displayed, and the representative image can be arbitrarily changed by adjusting a representative image position 86 by the user.

(Automatic Selection of Representative Image)

In order to automatically select the representative image, an image frame serving as a candidate of the representative image is selected from the moving image, and the moving picture waveform is calculated based on the candidate of the representative image. This is performed with respect to each image frame, and the moving picture waveform corresponding to each image frame is calculated. With respect to each moving picture waveform, a determination is made whether or not the waveform becomes periodic, or determination is made whether or not the cycle can be divided by a simple method such as a method by searching the threshold value, or minimum/maximum values. Thus, the moving picture waveform which is most suitable for dividing the cycle is specified and the basic image frame of the moving picture waveform is set as the representative image. At that time, a configuration may be such that a cycle to divide the moving image is found by autocorrelation which will be described later, and the cycle may be used to specify the most suitable moving picture waveform. Moreover, in addition to the image frame selected as the representative image, since there is almost the same image as this image frame in another cycle, the representative image may be determined such that the "almost the same image" in each cycle is extracted and the image is averaged based on a variation in each cycle.

According to a condition to select the "representative image" to divide the cycle, the waveform becomes periodic when the difference/similarity degree (evaluation value) is expressed as the waveform, and the cycle can be divided by the simple method such as the method by searching the threshold value or the minimum/maximum values. The determination whether or not the waveform becomes periodic can be made by shifting the waveform and determining whether or not a part in which the difference becomes small exists periodically. Regarding the determination whether or not the division of the cycle can be made by searching the threshold value or the maximum/minimum values, a method is used to determine whether or not the cycle actually obtained in the above way is the same as the cycle which has been obtained by the method to determine whether or not the waveform becomes periodic.

(Standard Timing Selecting Unit 31)

The standard timing selecting unit 31 selects the standard timing representing the cycle, to divide the input moving image obtained by the image obtaining unit with respect to each cycle. The standard timing selecting unit 31 selects the standard timing based on the representative image. As for the representative image, it may be automatically selected by the standard timing selecting unit 31, or certain image data can be selected by the user with the operating unit 55.

(Cycle Extracting Unit 32)

The cycle extracting unit 32 sections the input moving image with respect to each cycle, based on the standard timing selected by the standard timing selecting unit 31. Thus, since the picked-up input moving image can be periodically divided, the analyzing operation of the moving image by the user can be considerably reduced, and the analysis can be effectively made in analyzing the moving image containing a large amount of the image frames in the case of the high-speed camera especially.

(Cycle Adjusting Unit 33)

The cycle adjusting unit 33 may be provided to adjust the position of the cycle backward and forward before the input moving image is sectioned with respect to each cycle by the cycle extracting unit 32. Thus, the user can finely adjust the cycle by hand before the moving image is sectioned with respect to each cycle.

(Characteristic Amount Calculating Unit 34)

The characteristic amount calculating unit 34 calculates a characteristic amount of each frame or each frame group based on the input moving image obtained by the image obtaining unit. For example, the characteristic amount calculating unit 34 calculates the similarity degree between the representative image and each frame of the input moving image, as the characteristic amount, and the standard timing selecting unit 31 selects the timing which corresponds to the frame having the highest similarity degree in a certain period, as the standard timing. In addition, the characteristic amount calculating unit 34 may calculate a difference between the representative image and each frame in the input moving image, and the standard timing selecting unit 31 may select the timing which corresponds to the frame having the smallest difference in the certain period, as the standard timing.

(Image Trigger)

The similarity degree between the representative image and each frame during recording is calculated, and the time when the cycle is divided is recognized based on the similarity degree, as an image trigger, whereby the scene having periodic motion can be automatically divided with respect to each cycle with the phase aligned. That is, a trigger signal (image trigger) may be generated by a trigger generating unit in response to the standard timing. As the trigger generating unit, the above image processing section 30 may be used. The image trigger based on the representative image represents a specific phase in the scene having the periodic motion, and it can be used for the timing to divide the cycle. In addition, it may be used as an external trigger to instruct an external apparatus to perform inspection/operation when the abnormality is monitored or the image is inspected online, by supplying the trigger signal to the outside of the apparatus. Here, the external apparatus may be an image inspection apparatus to inspect the object with the image, or a processing apparatus to process the object. The external trigger is generated at the standard timing or after a certain time has elapsed from the standard timing.

In addition, while the description has been made of the case where the image inspection apparatus is the external apparatus here, the image process inspection apparatus may be incorporated. In this case, an image inspection such as flaw/defect extraction is performed for one or more images obtained at the standard timing or after the certain time has elapsed from the standard timing.

(Moving Picture Waveform Generating Unit 35)

The moving picture waveform generating unit 35 generates the moving picture waveform, based on the characteristic amount calculated by the characteristic amount calculating unit 34. The cycle extracting unit 32 determines the cycle based on the moving picture waveform, and can section the input moving image with respect to each cycle. Thus, a quantitative evaluation can be made based on the moving picture waveform, and the division can be easily made with respect to each cycle using the moving picture waveform.

When the moving picture waveform is obtained, the standard timing can be easily selected. For example, the standard timing selecting unit 31 defines the standard timing, using the time when the moving picture waveform exceeds the predetermined threshold value, as the standard timing. When each cycle is synchronized based on the standard timing, the division can be made with respect to each cycle without using a synchronous input.

(Moving Picture Waveform)

When the representative image is determined, the reference value is calculated based on the representative image, and the moving picture waveform (motion graph) is generated. More specifically, the reference value is calculated based on the difference/correlation in brightness or color difference between the representative image and the image of each frame of the moving image. Furthermore, the cycle of the moving picture waveform is determined and the moving image is divided with respect to each cycle. More specifically, the representative image which represents the cycle is selected in each cycle based on the moving picture waveform, and the previous and next frames are taken out based on the position of the representative image, so that the moving image can be divided with respect to each cycle with the phase aligned.

Figure 11:
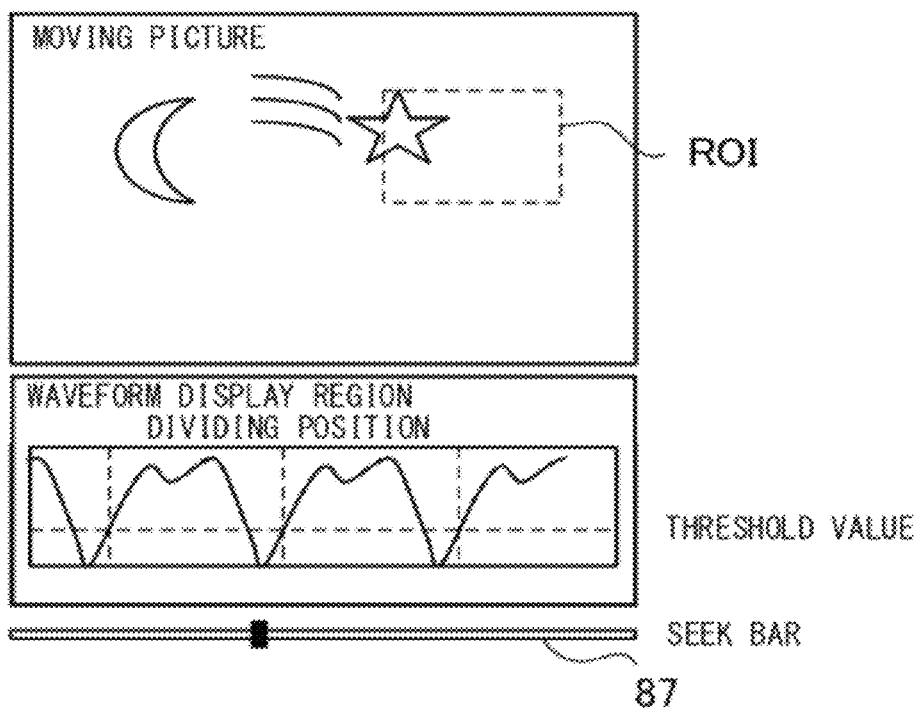
FIG. 11 is an image view showing an example to designate a target region in an image display region.

In addition, in calculating the moving picture waveform, only a part of the region of the image frame of the moving image can be used instead of using the whole of it. Referring to FIG. 11, a region designated by a broken line in the image display region 41 is set as a target region ROI (Region of Interest), and the image region used for calculating the reference value is limited to this part. Thus, when the image region is limited in this way and only the region containing necessary information is designated, an unnecessary image processing amount is saved, and the calculation process can be performed effectively at high speed with a low load. Especially, in a case where effective information to determine the cycle is contained in a part of the image frame, this method is effective.

Conventionally, there has been no technique or idea to divide the moving image periodically, and only a switching part in the imaging operation between different dates (a previous recording end position and a next recording start position) is detected. That is, it has not been performed to detect periodicity from the continuous moving image picked up at the same date and cut the moving image with respect to each cycle.

A method to recognize a periodic motion of the object in the moving image of the one or more objects and calculate its cycle includes a method using autocorrelation in a difference matrix. According to this method, a difference matrix of N×N representing a difference between m (=1, 2, . . . , N)th frame and n (1, 2, . . . , N)th frame (m-th row and n-th column shows a difference value or a similarity degree between the m-th frame and n-th frame) is generated based on a N-frame moving image. The difference matrix of N×N is similarly treated as the image of N×N, and the correlation is found by the same method as the autocorrelation of the image, and the cycle can be calculated based on a shifted amount having the high autocorrelation in a XY direction (frame interval in this case). Here, the autocorrelation of the image is a method in which the same image is shifted in the XY direction little by little to find its correlation. In this case, the representative image is identified as the searched image in template matching. According to this method, an average cycle of the periodic motion existing in the N-frame moving image can be calculated, but each cycle cannot be found when there is a variation in cycle, so that the problem is that when the M-frame moving image (N<M) is divided based on the average cycle found in the N frames, an error between the average cycle and the actual cycle is accumulated.

In addition, there is another method in which a periodic waveform such as AC waveform is divided with a trigger and displayed by oscilloscope with respect to each cycle. According to this method, by appropriately setting the trigger, the division can be made with respect to each cycle with the phase of the waveform aligned. Meanwhile, according to an image trigger technique which is also known, a reference value such as an average brightness value is calculated based on the image data to form a waveform and a trigger is applied thereto. By combining the above techniques, the periodic moving image can be divided, but the cycle cannot be correctly recognized in some cases depending on the method for calculating the reference value, so that it is difficult to apply a correct trigger. For example, when there is a scene in which the brightness changes during the operation of one cycle of the object, the trigger using the brightness value as the reference value is not appropriate.

Meanwhile, according to this embodiment, the image representing the cycle is selected as the representative image as described above, the reference values is calculated based on the representative image, and the moving picture waveform is generated. According to this method, the waveform can be stable against a luminance change. In addition, since the standard timing for the cycle division is determined by the moving picture waveform provided based on the representative image, the moving image having the same phase in each cycle, that is, synchronous moving image can be extracted. Thus, fluctuation of the cycle can be easily corrected, and the problem in error accumulation due to the average cycle can be solved. In addition, when the moving picture waveform does not come across the threshold value in the certain period or longer, it is determined that the cycle is shifted, and the cycle is abnormal.

(Moving Image Observing Program)

According to the Moving Image Pickup Operation, the Operation of the user is received, the moving image is picked up, displayed, and analyzed by the moving image observing program. The moving image observing program is incorporated in the moving image pickup apparatus in the example shown in FIGS. 1 and 2, while as another configuration, a general-purpose computer is connected to the moving image pickup apparatus, the moving image observing program is installed into the computer, and the operation is performed to the moving image pickup apparatus. In this case, the displaying unit 52 and the operating unit 55 may be provided as a monitor and a pointing device such as a touch panel, a mouse, or a keyboard of the computer.

Figure 3:
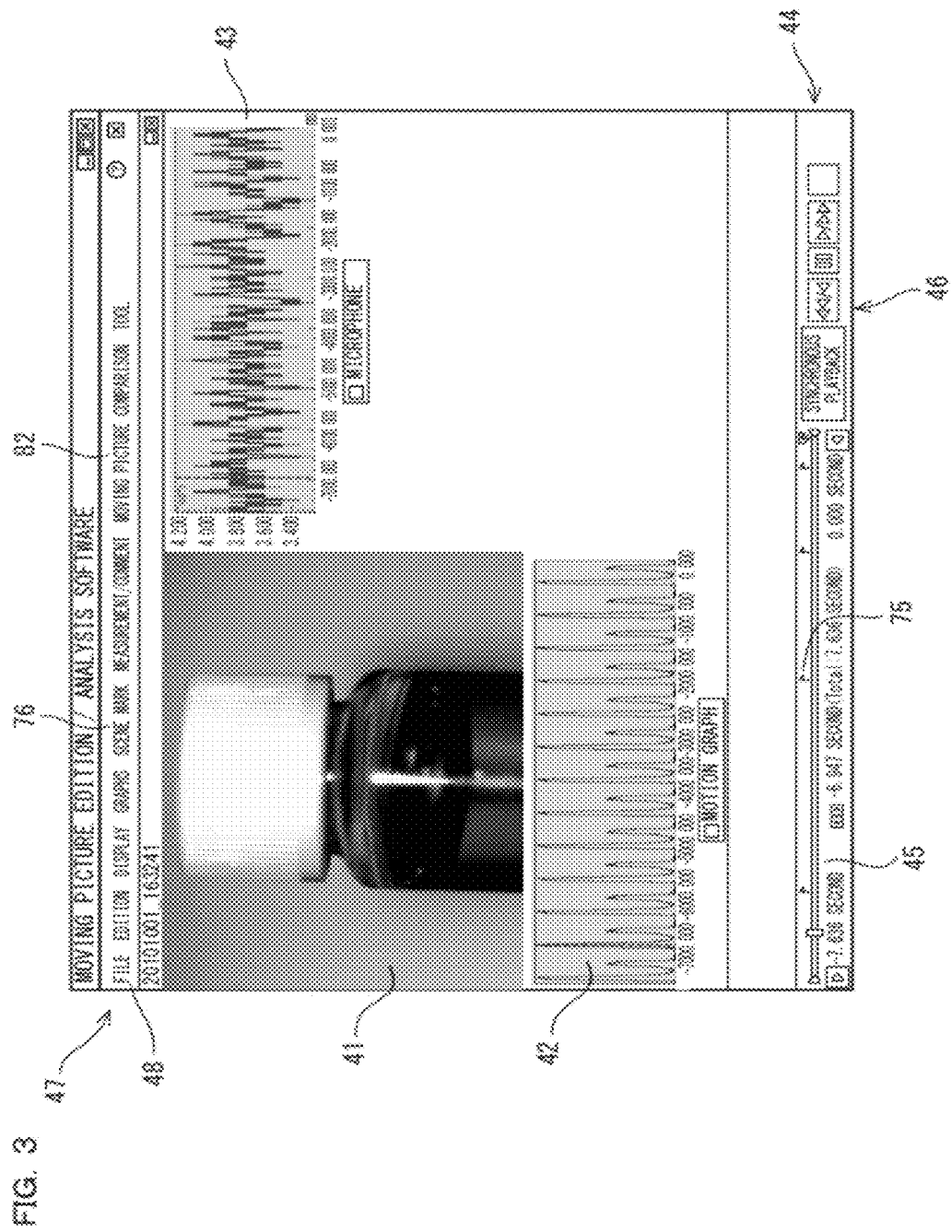
FIG. 3 is an image view showing a user interface screen of a moving image observing program.

FIG. 3 shows a user interface screen of the moving image observing program. The moving image observing program shown in this figure provides an image display region 41 to display the moving image, and a waveform display region 42 to display the moving picture waveform which will be described later. In this example, the image display region 41 is provided in an upper left part of the screen, and the waveform display region 42 is provided under that, but this arrangement is just one example, and various layouts can be employed. For example, the image display region may be displayed in a different window.

(External Signal Display Region 43)

On the right side of the image display region 41, an external signal display region 43 is provided to display a waveform of an external signal stored at the same time as the time when the moving image is recorded. The external signal includes an input signal from various kinds of sensors such as a temperature sensor, a distance sensor, a pressure sensor, an acceleration sensor, or a microphone.

(Synchronous Recording of Moving Image and External Signal)

Figure 4:
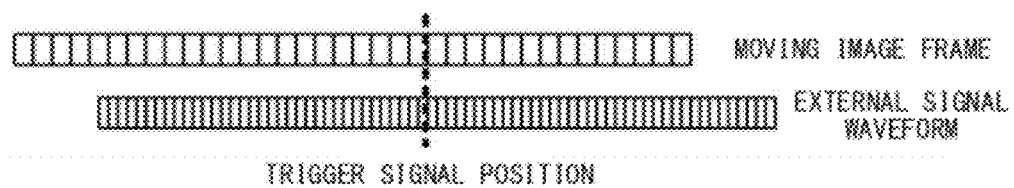
FIG. 4 is a schematic view showing a behavior in which a moving image and a waveform of an external signal are synchronized and recorded.

When the Moving Image is Picked Up by the Imaging Unit 10, the waveform of the external signal can be recorded in synchronization with its recording. For example, as shown in FIG. 4, a time is synchronously recorded by an electric trigger signal. The trigger signal is generated in response to a button input by the user, an input from a sequencer, at a moment (image trigger) when the waveform of the sensor becomes more/less than the threshold value, or at a moment when the brightness of the moving image becomes more/less than the threshold value. As for each of the moving image and the external signal waveform, the recording is set so as to be performed for several frames (samples) before triggered or several frames after triggered. Especially, the one in which the number of recording frames before triggered is set to 0 is called a start trigger, and the one in which the number of recording frames after triggered is set to 0 is called an end trigger. In addition, when the frame is recorded in the memory serving as the primary memorizing unit 53, a ring buffer is used, that is, the recording is performed until the set memory runs out before the trigger is applied, and when the memory runs out, an old frame is sequentially replaced with a most recent frame. In addition, the number of the moving image frames and the number of waveform samples, per unit time do not always coincide with each other.

(Playback Control Field 44)

A playback control field 44 is provided in a lower part of the waveform display region 42 to mainly designate a position of the moving image. The playback control field 44 has a seek bar 45 and a playback button group 46. The seek bar 45 is provided in a lower part of the waveform display region 42, and it corresponds to a length of the moving image and shows a current playback position, and the position can be changed to a designated position by a click or drag of the mouse. In addition, the playback button group 46 is provided on the right side of the seek bar 45, and has a forward playback/fast-forward button, a reverse playback/fast-reverse button, a pause button, and a playback speed designation button.

(Tool Bar 47)

Figure 5:
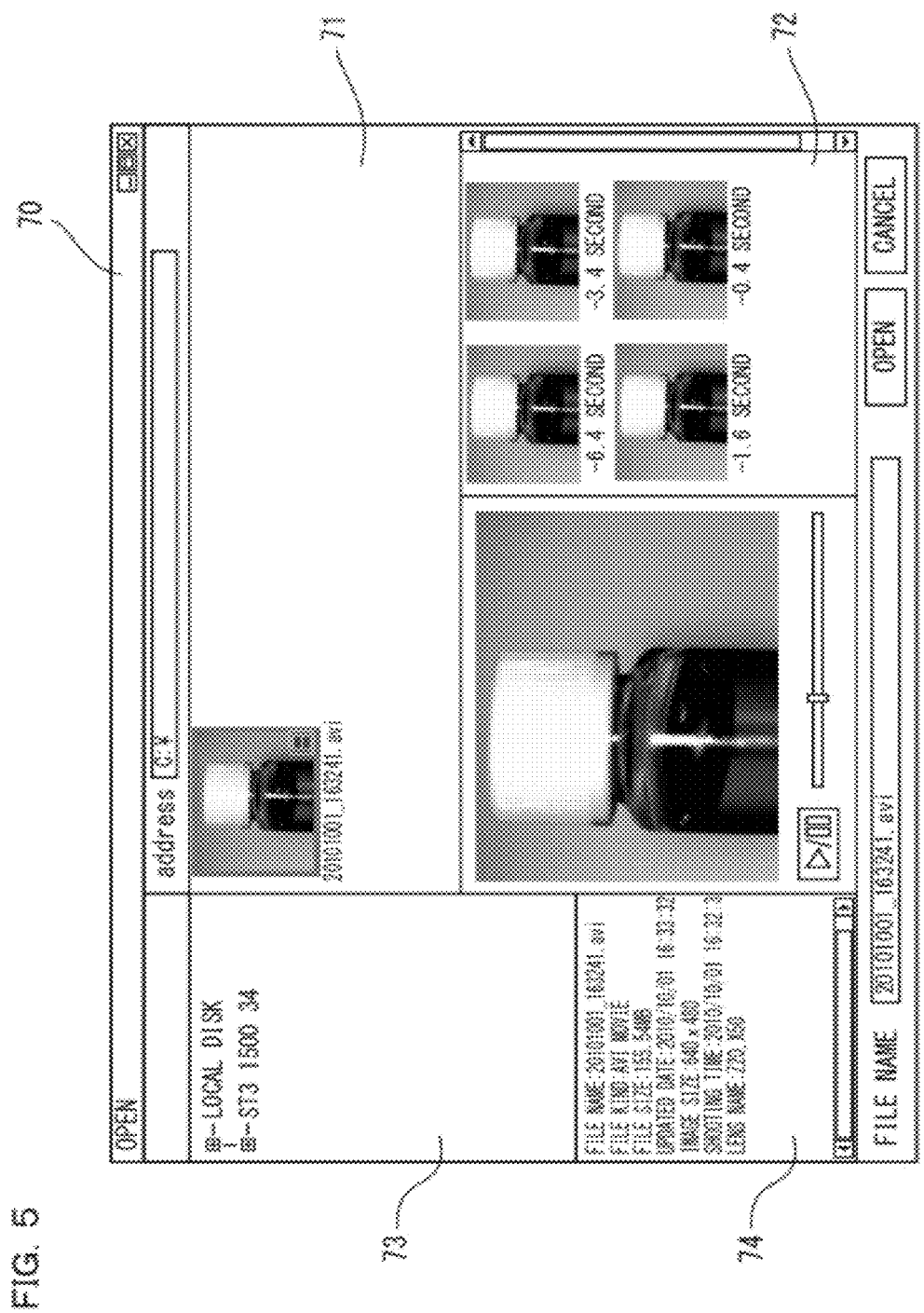
FIG. 5 is an image view showing a file selecting dialog.

A tool bar 47 having buttons to perform various kinds of operations is arranged in an upper part of the screen. A "file" button 48 is provided at a left end of the tool bar 47 and may serve as the moving image obtaining unit for reading the inputted moving image data which has been already recorded by the imaging unit 10. In addition, the input moving image picked up by the imaging unit 10 may be directly taken in the moving image observing program. When the "file" button 48 is pressed, a file selection dialog 70 shown in FIG. 5 appears, and the user selects a desired data file from the input moving image data which have been already stored. According to the example in FIG. 5, a file list 71 is displayed in an upper right part of the screen, and a preview of the selected moving image data is displayed in a preview display field 72 in a lower right part of the screen. In the preview display field 72, the moving picture is displayed on the left side, and an image frame list of the moving image in representative positions is displayed on the right side. In this example, in accordance with a chapter which has been previously set in the moving image data, the image frame corresponding to a position of the chapter is displayed. Furthermore, on the left side of the file selection dialog 70, a file tree 73 to select the file is displayed in an upper part, and detailed information 74 of the moving image file which is being currently selected is displayed in a lower part. The detailed information 74 includes a file name and a shooting date, an image size and a shooting condition (such as a lens, a magnification, or a device name used in shooting) in shooting, and a comment.

Thus, when the input moving image data is selected in the file selection dialog 70, as shown in FIG. 3, the moving picture of the selected moving image data is displayed in the image display region 41, and the waveform of the external signal simultaneously recorded when the moving image data is picked up is displayed in the external signal display region 43. In the example in FIG. 3, a waveform of voice recorded with a microphone is displayed as the external signal waveform.

In addition, in this example, at the time of creation of the moving image, the chapter described above can be set, and the data of the external signal simultaneously recorded can be buried, or linked to an external data file. The moving image observing program also has such function to create the data file, so that the data file is stored in a desired format by pressing the above "file" button 48 and selecting a storage menu, whereby the data file can be created.

(Chapter Setting Function)

The moving image observing program can set a chapter at any position so that the desired position can be easily searched. The chapter can be added, changed, and deleted. In the example in FIG. 3, the chapter which has been already set in the moving image data is displayed in a flag 75 provided above the seek bar 45 in the playback control field 44. When the arbitrary flag 75 is selected, a jump is made to this flag position.

(Scene Mark List Window 77)

Figure 6:
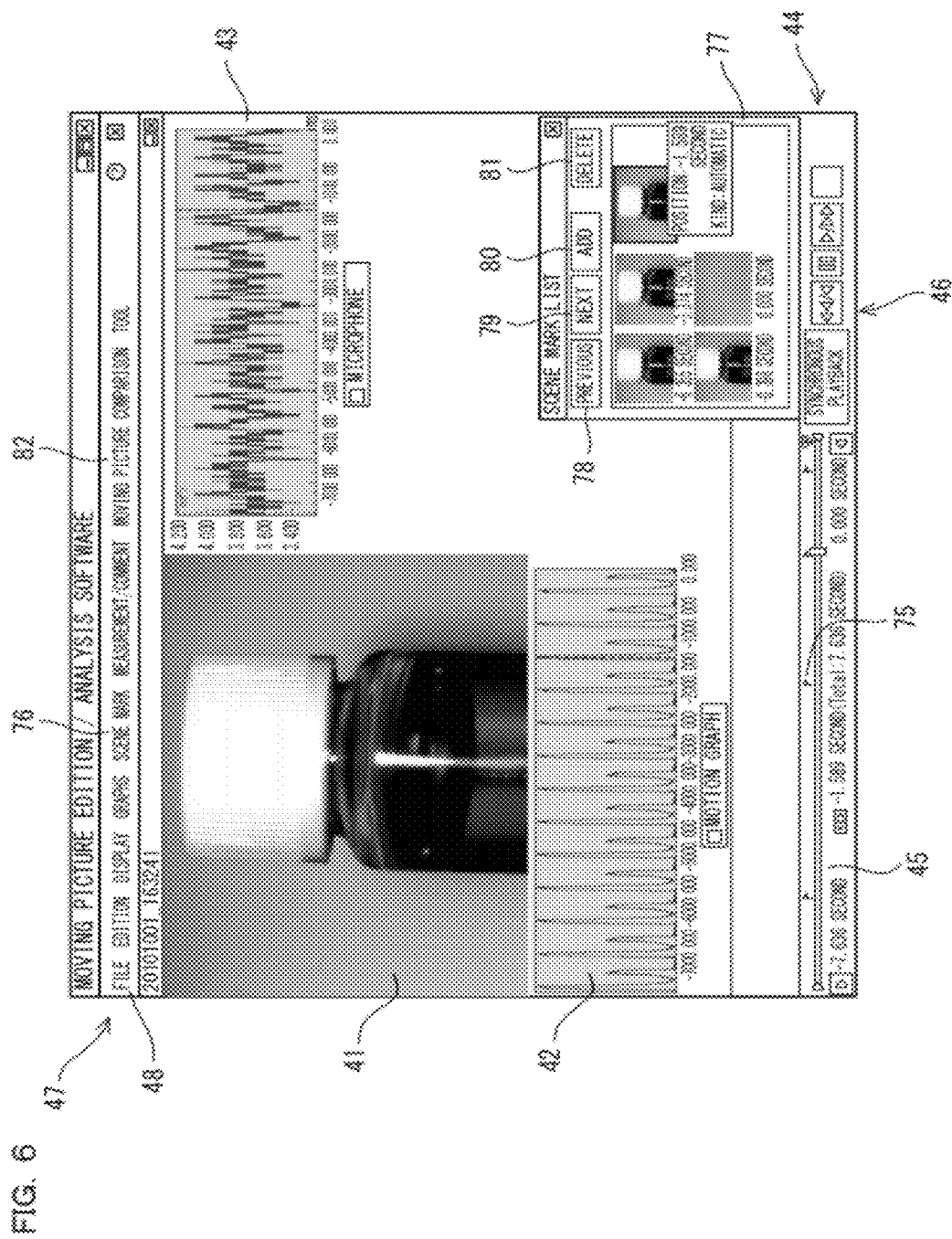
FIG. 6 is an image view showing a scene mark list window.

Furthermore, a list of the image frame corresponding to the chapter position can be displayed. More specifically, when a scene mark button 76 of the tool bar 47 is pressed, a scene mark list window 77 shown in FIG. 6 is displayed. The scene mark list window 77 shows the frame list corresponding to the position of the chapter set in the moving image data which is currently being displayed. When the desired image frame is selected in the scene mark list window 77, a jump is made to the designated chapter position. In addition, when a "previous" button 78 or a "next" button 79 is pressed, a jump is made from the current position to a recent chapter position. When an "addition" button 80 is pressed in an arbitrary position, a new chapter is added to the current position. As for the added chapter, an image frame corresponding to the chapter position is added in the scene mark list window 77. In addition, when the chapter is to be deleted, the image frame corresponding to the chapter to be deleted is selected and a "delete" button 81 is pressed. In addition, as shown in FIG. 6, information of the chapter pointed by a mouse cursor can be displayed in the window by a tool chip function.

(Automatic Chapter Setting Function)

The chapter can be automatically added as well as being manually set by the user. In the example in FIG. 6, when a "scene mark" button of the tool bar 47 is pressed, and an "automatic scene mark" menu is selected, the moving image observing program automatically analyzes the moving image file and sets the chapter. As for a method for setting the chapter, a change point of the scene may be detected by the image processing, or the chapter may be added at certain intervals. Thus, the chapter can be set automatically or manually, which assists retrieving and analyzing operations of the moving image data having great amount of data especially.

(Moving Picture Dividing Function)

Furthermore, the moving image observing program has a moving picture dividing function to divide the moving image data with respect to each cycle. Hereinafter, a description will be made of a procedure to divide the input moving image with the phase aligned with respect to each cycle using the moving picture dividing function, with reference to FIGS. 7 to 12.

(Target Zone Designation Screen 83)

Figure 7:
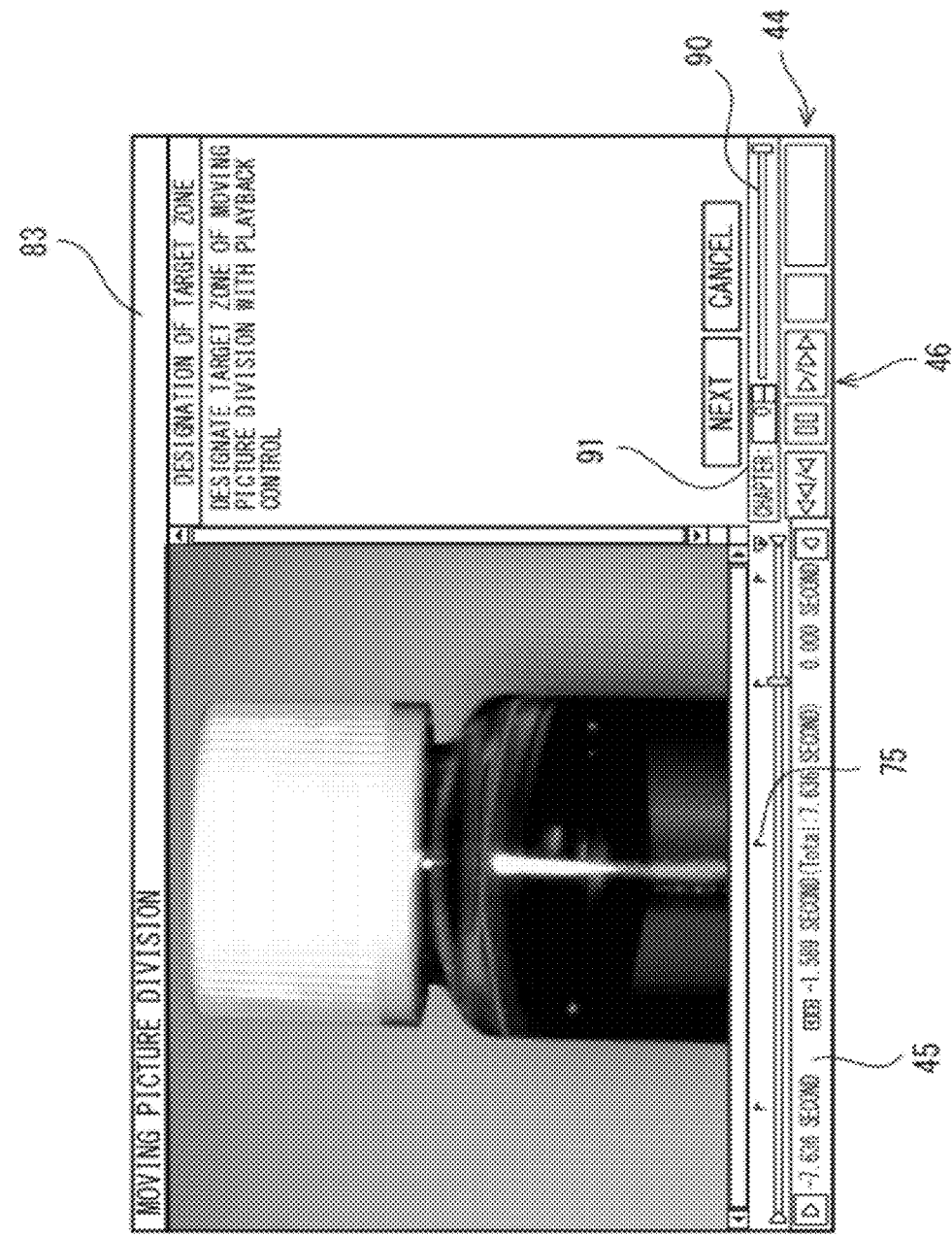
FIG. 7 is an image view showing a target zone designating screen.

First, a "moving picture comparison" button 82 is pressed in the tool bar 47 and a "moving picture division" menu is selected. Then, as shown in FIG. 7, a screen 83 to designate a zone of a division target is displayed. The user designates a range of the moving image to be divided, from the target zone designation screen 83 with the seek bar 45 when needed.

(Representative Image Designation Screen 84)

Figure 8:
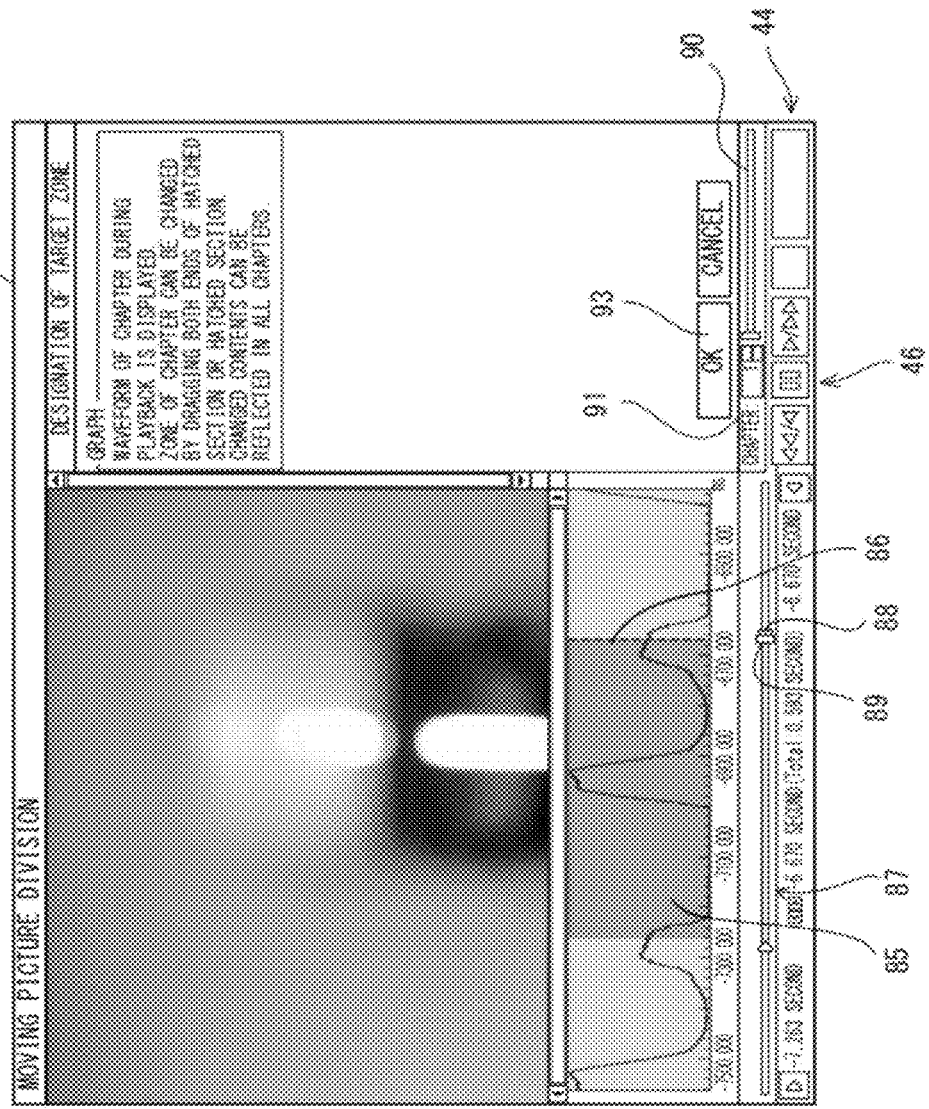
FIG. 8 is an image view showing a representative image designating screen.
Figure 9:
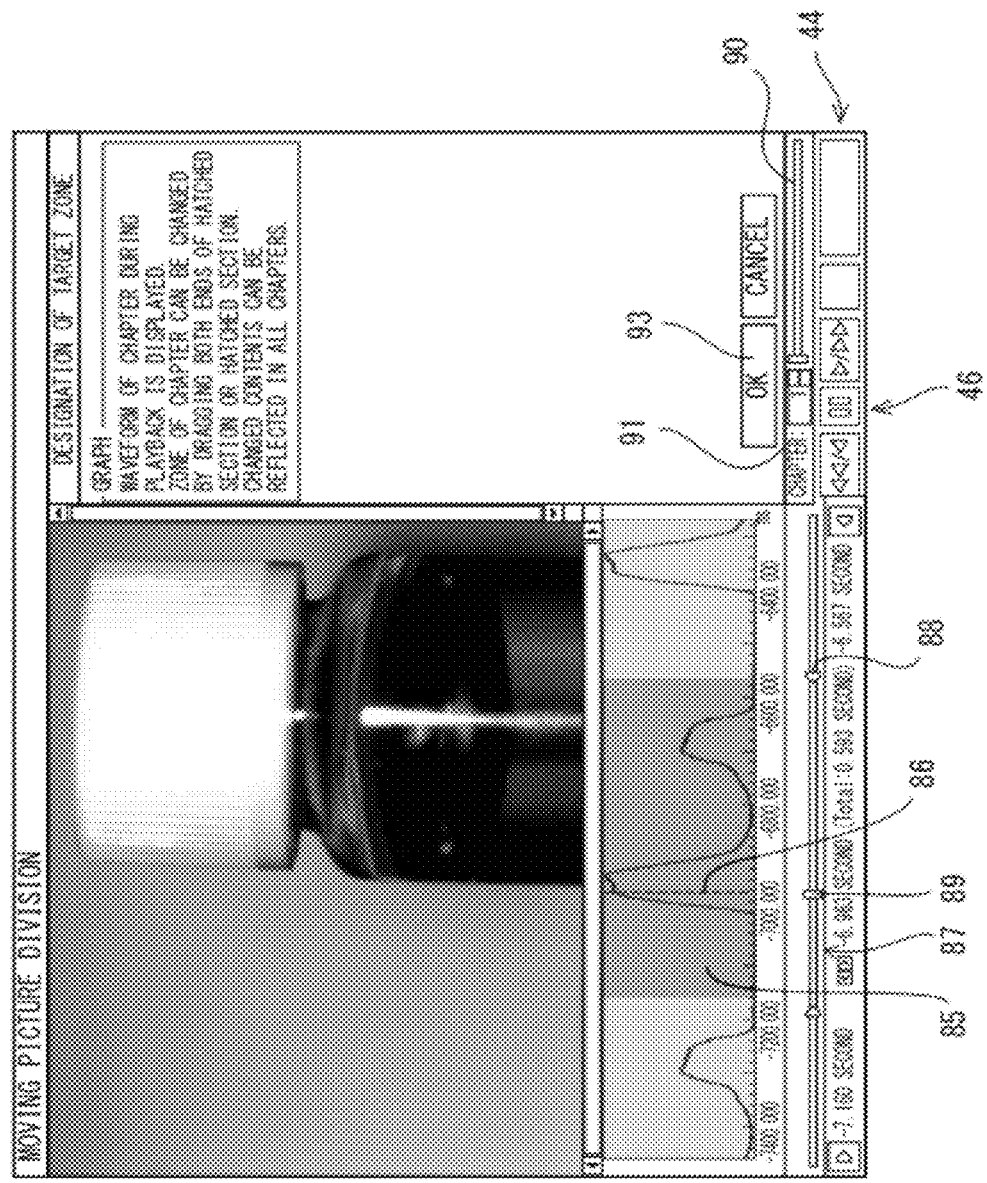
FIG. 9 is an image view showing an example to adjust a region for one cycle.

After the target zone has been designated, when the "next" button is pressed, a representative image designation screen 84 shown in FIG. 8 appears, and one cycle which has been automatically selected is designated. On this screen, the moving picture waveform (this is also called a motion graph in FIG. 8 and will be described in detail later) is displayed in the waveform display region 42, and a region 85 corresponding to one cycle calculated by the cycle extracting unit 32 is displayed in a hatched manner. The region 85 corresponding to the one cycle is automatically set by the cycle extracting unit 32. The region 85 corresponding to the one cycle can be moved to right and left with its width maintained in the waveform display region 42, and by dragging the region 85 corresponding to the one cycle, a start position and an end position of the one cycle can be adjusted as shown in FIG. 9

Figure 10:
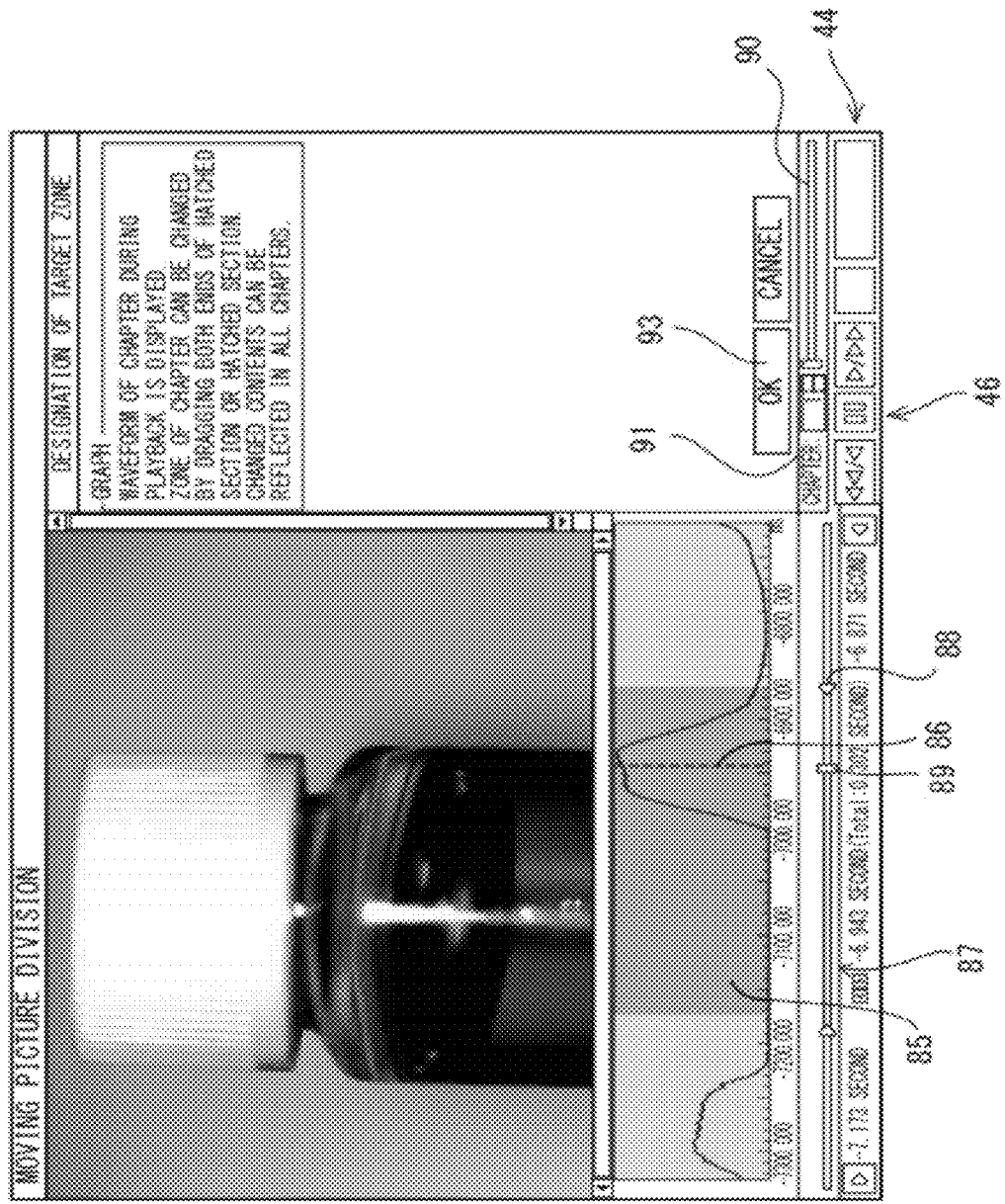
FIG. 10 is an image view showing an example to adjust an end position of the one cycle.

In addition, the start position and the end position of the cycle can be individually changed. For example, when the end position is narrowed by dragging it with the mouse from a state shown in FIG. 9, a zone shorter than the one cycle can be designated as shown in FIG. 10. Similarly, the start position of the cycle can be changed, so that the start position and the end position of the cycle are changed to any position, and consequently, the start position, and the end position of the one cycle, and a length of the cycle can be arbitrarily adjusted.

(Representative Image Position 86)

In Addition, a Position Shown by a Broken Vertical Line in the Waveform display region 42 represents a representative image position 86 which shows the position of the image frame which is being currently displayed in the image display region 41, and this representative image position 86 can be also arbitrarily changed. The image frame at the position selected here is selected as the representative image. Thus, the vertical line functions as a representative image selecting unit to select and change the representative image.

(Phase Adjusting Seek Bar 87)

In addition, on the representative image designation screen 84, the seek bar in the playback control field 44 provided under the waveform display region 42 is a phase adjusting seek bar 87, and can seek a desired position in the cycle. More specifically, the length of the seek bar almost conforms to the waveform display region 42, and corresponds to the moving picture waveform which is currently being displayed in the waveform display region 42. That is, a stopper 88 is displayed on the phase adjusting seek bar 87 and corresponds to each of the start position and the end position of the region 85 corresponding to the one cycle, and only a zone defined here can be subjected to playback, fast-forward, and reverse playback with the playback button group 46. In addition, a slider 89 provided on the phase adjusting seek bar 87 corresponds to a position of the representative image position 86, and the representative image position 86 can be adjusted by operating the slider.

(Cycle Switching Slider 90)

In Addition, a Cycle Switching Slider 90 to Switch the Cycle of the displayed moving image is provided on the upper side of the playback control field 44. Unlike the seek bar, the cycle switching slider 90 provided on the screen in FIG. 8 corresponds to a whole length of the moving image and shows the currently displayed position. In addition, it responds to the motion of the chapter described above, and when the chapter number in a chapter designating field 91 is changed, the position can be switched to the designated chapter position. When the chapter number of the chapter designating field 91 is switched, a jump is made to the corresponding chapter. In addition, at this time, other than a head or end position of the chapter after moved, the jump may be made to a position in the same phase in the chapter after moved so as to correspond to a phase position displayed in the previous chapter. Thus, with the cycle switching slider 90, the user can confirm whether or not the cycle is correctly divided in another position of the moving image data.

Thus, the example in which the user manually selects the representative image has been described. Meanwhile, in the case where the representative image is automatically calculated, the image having a similar image is automatically selected one by one in each cycle calculated by the autocorrelation. For example, an image having a peak in the moving picture waveform is set as the representative image.

(Correction of Standard Timing)

In addition, the standard timing of the cycle set as described above does not always coincide with the start or the end of each cycle. Therefore, it is necessary to separately set a range from the start to the end of the cycle, as the standard timing. For example, in a case of a process repeated such that a product enters a production line, is subjected to a treatment, and leaves there, the standard timing can be set at the entering part, the treatment part, or the leaving part. In this case, the user may set the entering part as the start of the cycle, and the leaving part as the end of the cycle, or may set only the treatment part as one cycle.

Figure 12:
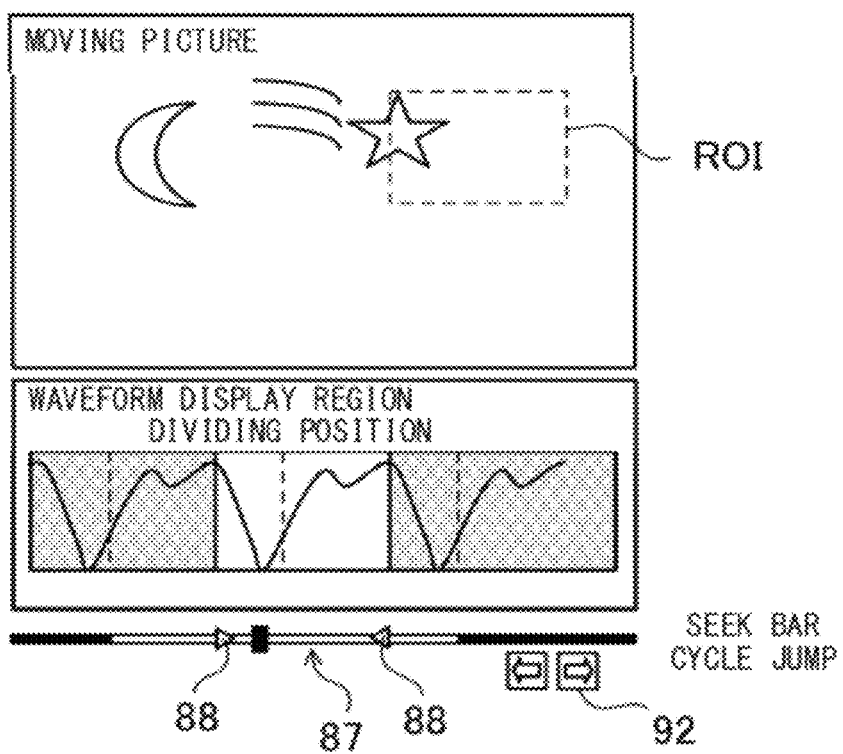
FIG. 12 is an image view of the user interface screen to set a start and an end of the cycle.

FIG. 12 shows one example of the user interface screen to set the start and end of the cycle. On this screen, the phase adjusting seek bar 87, and the stopper 88 which sets the start/end of the cycle are moved from the center of the division position toward the previous and next division positions, and set the start/end of each cycle based on the division position as relative positions thereto. The user makes this setting while viewing the moving image having the one cycle. In order to confirm that which cycle is used for the division, the cycle can be moved by a cycle jump button 92. When the cycle jump button 92 is pressed, the displayed cycle is moved backward and forward, so that it is confirmed that whether or not there is a problem when the division setting made in one cycle is applied to another cycle. In addition, at this time, the waveform of the cycle can be superimposed and displayed.

In addition, there is a case where a variation is generated in the start/end timing in each cycle. Since such variation appears in the waveform, the superimposed display of the waveforms is observed and the start/end positions of the cycle can be determined based on the variation.

Figure 13:
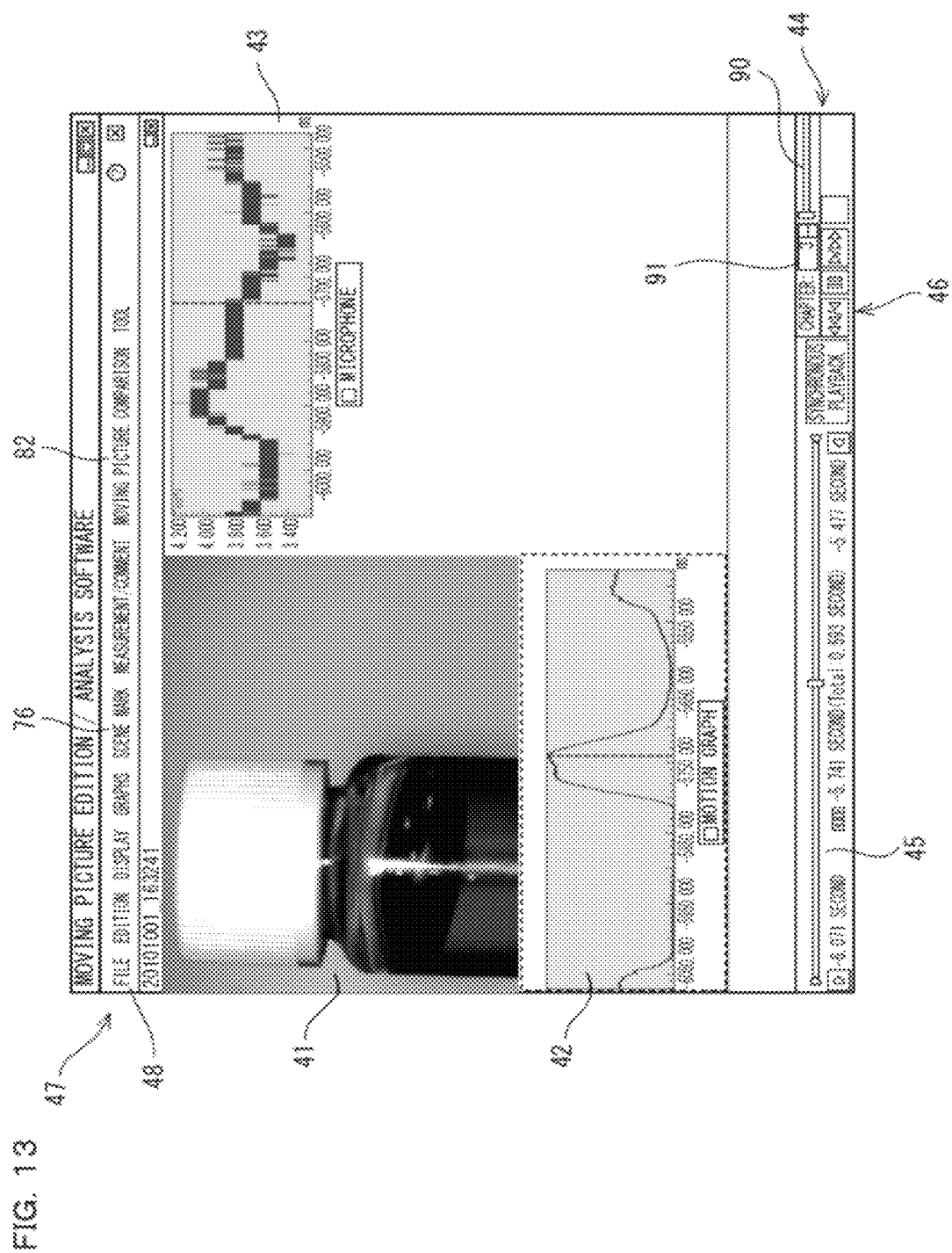
FIG. 13 is an image view showing the user interface screen of a divided moving image.

Thus, after the representative image and the start position and end position of the cycle have been determined, when an "OK" button 93 on the screen in FIG. 8 is pressed, the moving image is divided into the divided moving images with respect to each cycle and displayed on a screen in FIG. 13. In addition, the division of the moving image does not always mean that the moving image data is divided, but it includes a condition that the divided moving image can be identified with respect to each cycle, on the screen of the moving image observing program. For example, the division of the moving image in this specification also includes a configuration in which the chapter is added with respect to each cycle and the moving image is switched to a desired divided moving image by switching the chapter.

As shown in FIG. 13, in the waveform display region 42, the moving picture waveform of the divided moving image in the designated chapter is shown. On this screen, the cycle switching slider 90 and the chapter designating field 91 are provided similarly to FIG. 8, and the chapter can be switched to the desired chapter by operating these.

In addition, in the case where the moving image and external signal waveform such as the sensor input are synchronously taken in, they can be used for abnormality monitor recording which will be described later, by dividing them with respect to each cycle, and evaluating a degree of similarity of the sensor waveforms using correlation while taking the phase timing with the image.

(Analyzing Function)

As described above, the moving image can be divided with respect to each cycle, so that the moving image data containing the great amount of image frames can be easily processed and analyzed by comparing to the image frame of each phase in each cycle. Especially, the divided moving images provided with its phase aligned can be easily compared with respect to each phase, which is advantageous in analysis. A description will be made below of an example of an analyzing unit to analyze the divided moving images with its phase aligned.

(Moving Picture Comparing Function)

Figure 14:
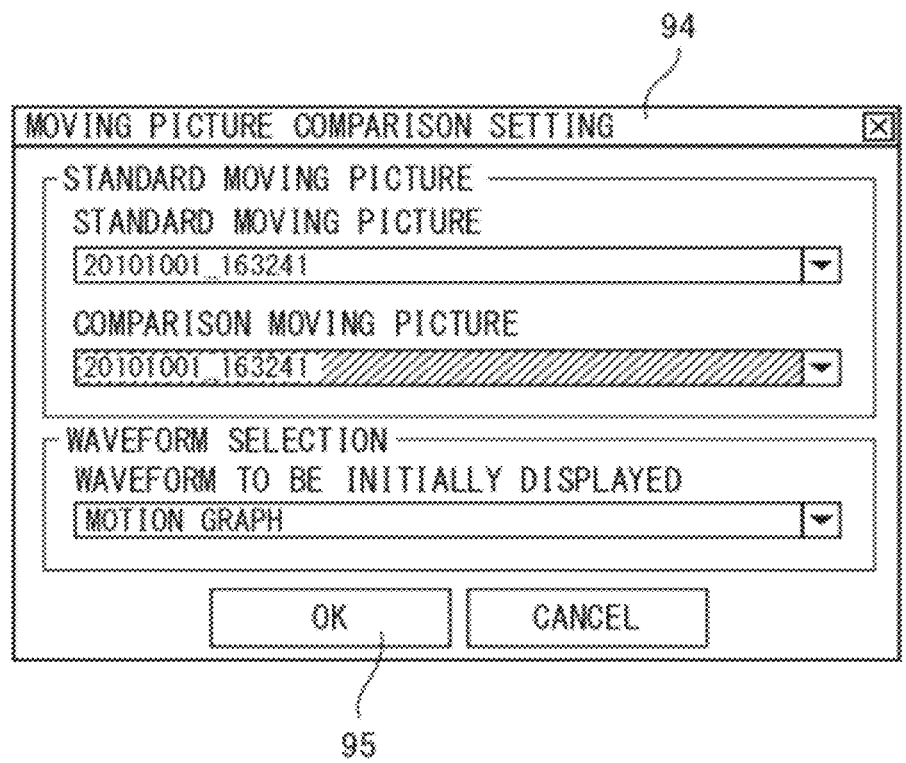
FIG. 14 is an image view showing a moving picture comparison setting screen.
Figure 15:
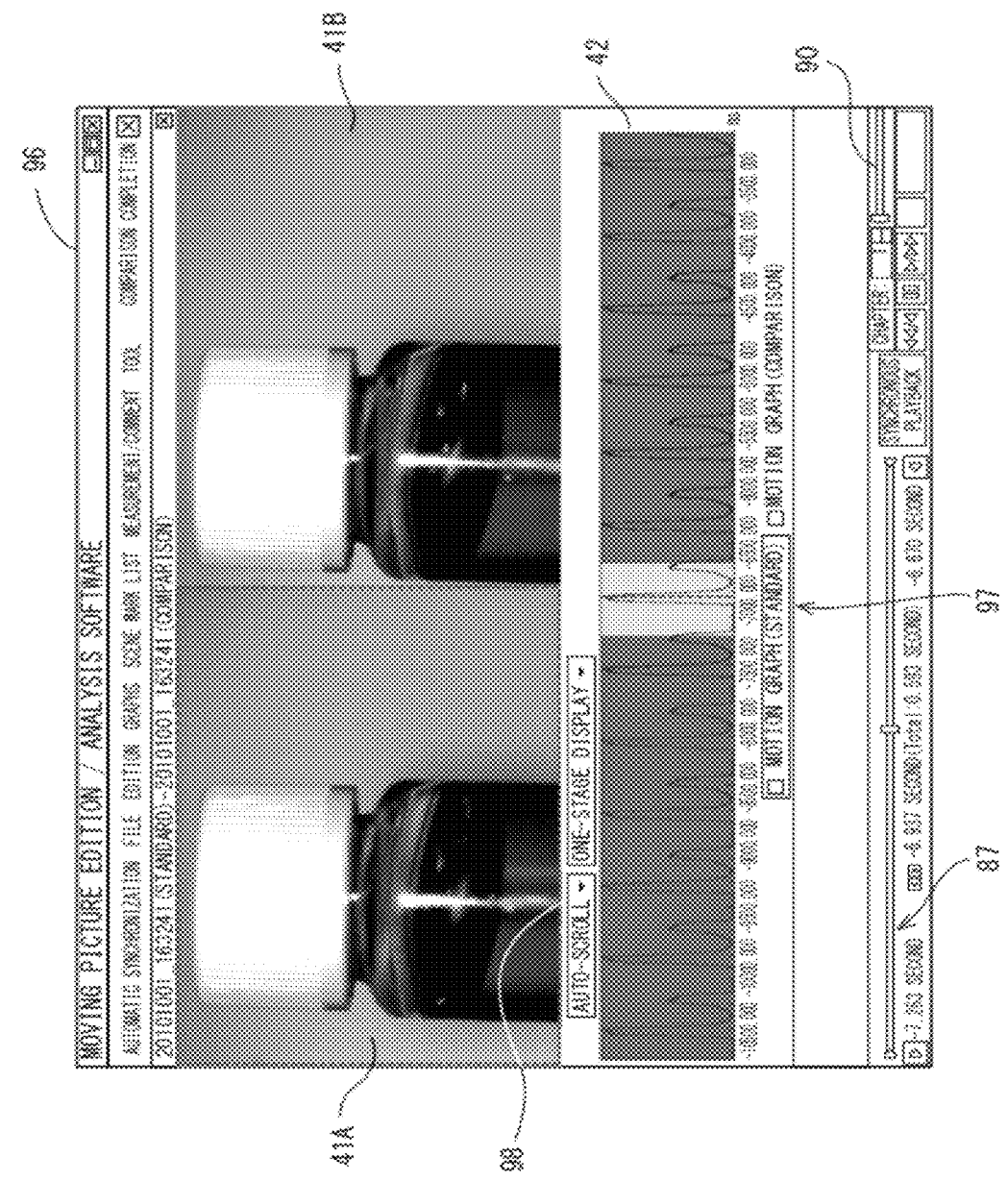
FIG. 15 is an image view showing a moving picture comparison screen.

First, a description will be made of a moving picture comparing function to compare the divided moving images divided as described above, as one analyzing function, with respect to FIGS. 13 to 16. On the screen in FIG. 13, a "moving picture comparison" menu is selected from a "picture comparison" button 82 in the tool bar 47. Then, a moving picture comparison setting screen 94 is displayed as shown in FIG. 14, in which a standard moving picture and a moving picture of a comparison target are each designated. In addition, as a waveform to be initially displayed in the waveform display region 42, the moving picture waveform (motion graph) or another signal waveform can be selected. After the selection, when an "OK" button 95 is pressed, a moving picture comparison screen 96 is displayed as shown in FIG. 15. On this moving picture comparison screen 96, the image display region 41 is divided into left and right 41A and 41B in an upper stage, in which selected moving images are displayed. In this example, the standard moving picture and the comparison moving picture are displayed on the left side 41A and right side 41B, respectively, but they may be exchanged. In addition, the waveform display region 42 is provided in a middle stage with its length elongated to right and left. The moving picture waveform displayed in the waveform display region 42 is switched by a selection button 97 provided in a lower part of the waveform display region 42. In this example, the moving picture waveform of the standard moving picture is shown. In addition, in response to the selection button 97, the moving picture waveform which is the operation target of the lower slider and playback button 46 in the playback control field 44 can be also switched. In addition, without using the selection button 97, the operation can be switched to the operation of the selected moving image by directly clicking the image display region 41. In addition, when the moving image is switched, the phase adjusting seek bar 87 and the cycle switching slider 90 are moved to the position corresponding to the moving image.

Figure 16:
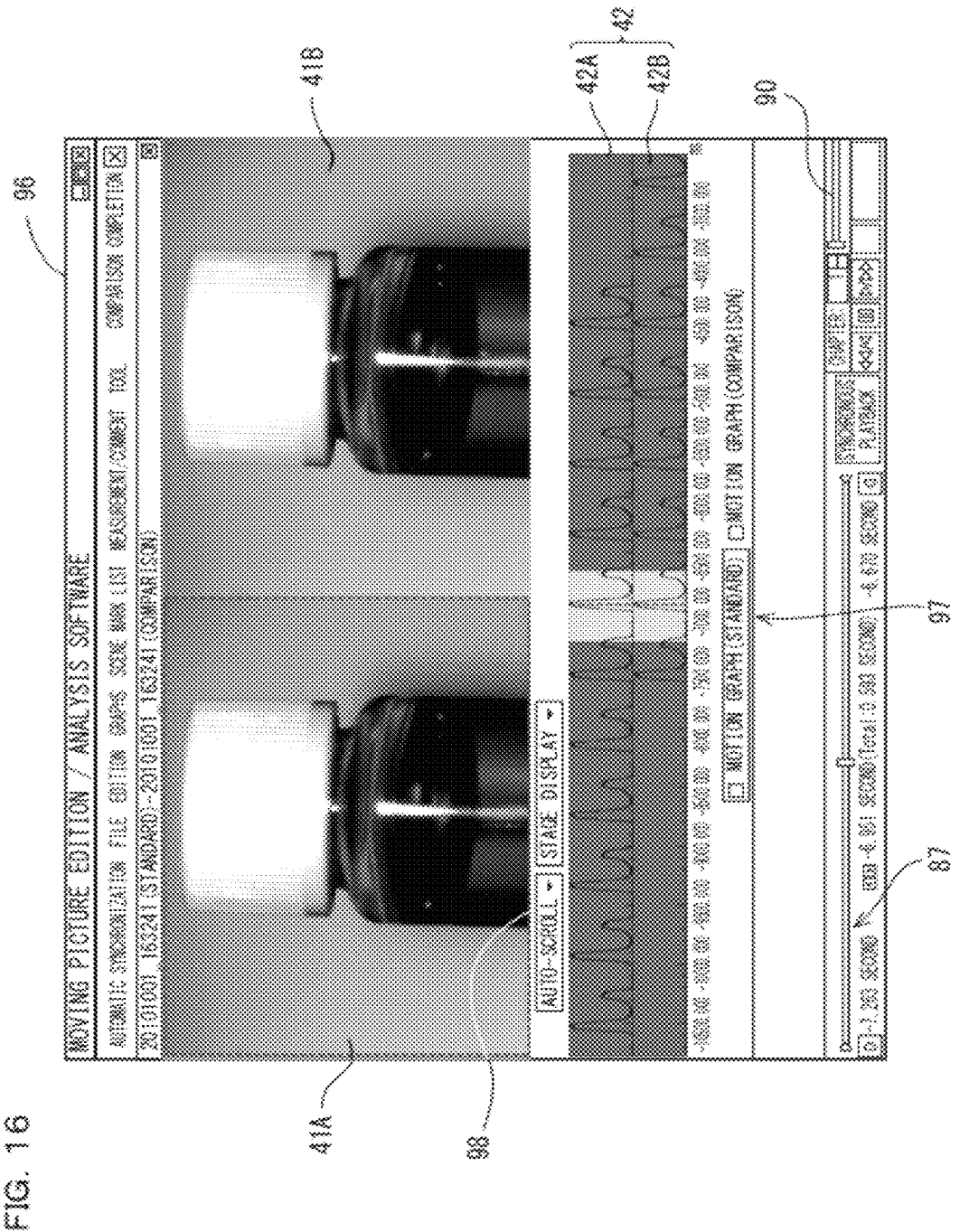
FIG. 16 is an image view showing an example in which a waveform display region is multiple-stage display.

In addition, the waveform display region 42 can be displayed in a multiple-stage manner. In an example shown in FIG. 15, when a "one-stage display" button 98 provided in an upper left part of the waveform display region 42 is pressed to switch the display to a "multiple display", as shown in FIG. 16, the waveform display region 42 is divided into upper and lower regions 42A and 42B, and switched to the multiple display. In this example, the moving picture waveforms of the standard moving picture and the comparison moving picture are displayed in the upper stage 42A and the lower stage 42B, respectively.

Furthermore, a function may be such that when the position of one moving image is designated on the waveform display region 42, a jump can be made to a part in the same phase of the other moving image. Thus, this is very convenient for the comparison and analyses in the same phase.

In addition, as the standard moving picture and comparison moving picture, the different moving pictures are designated, but other than that, the same moving picture can be designated. In this case, the different cycles of the same moving image can be displayed on the same screen and the comparison can be made with respect to each cycle with the phases aligned.

(Moving Body Following Function)

Figure 17:
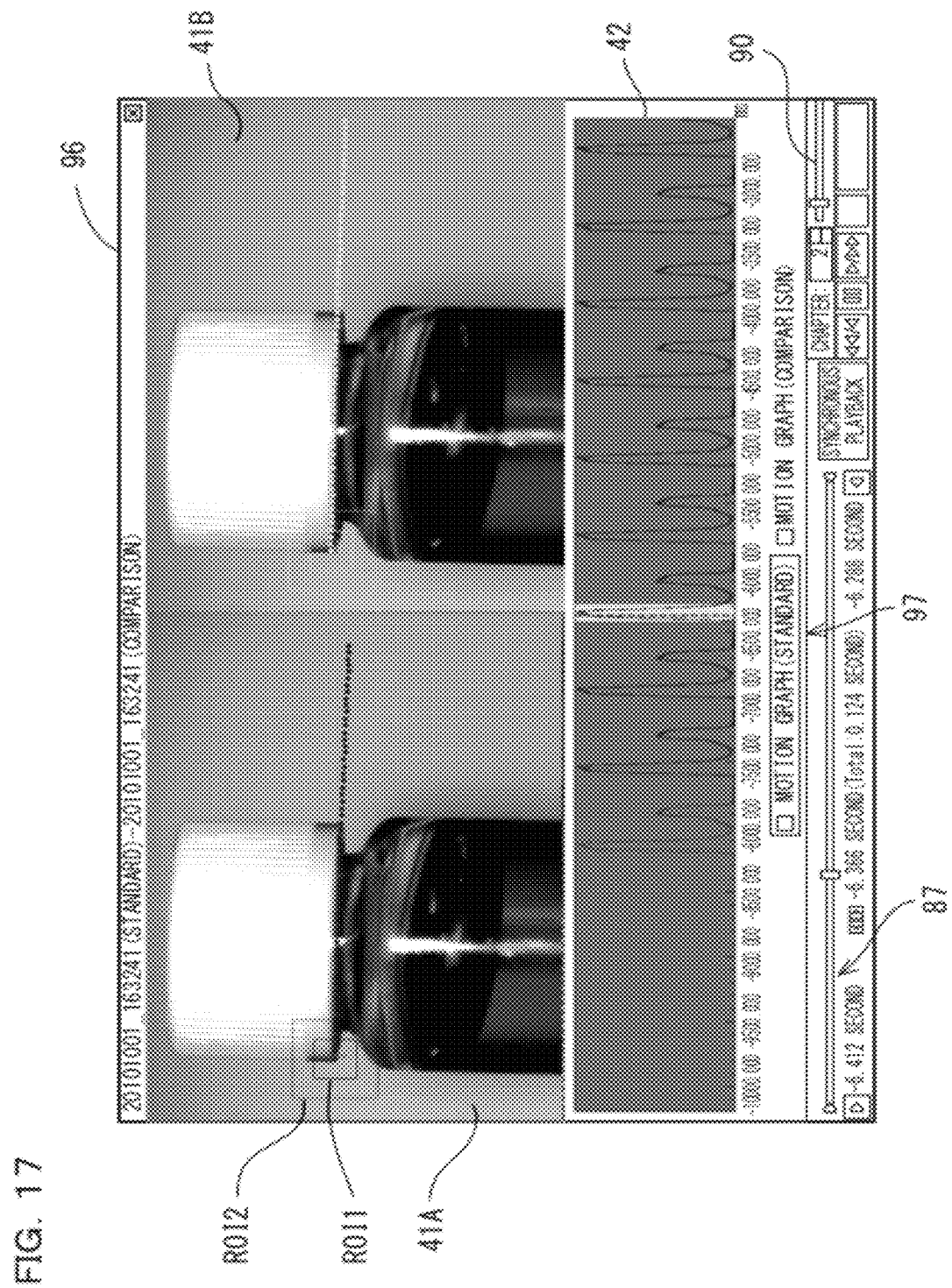
FIG. 17 is an image view showing a behavior to execute a moving body following function.

As another example of the analyzing function, the moving image observing program has a moving body following function to show transition of the image which is similar to the designated image. FIG. 17 shows an example in which the moving body following function is executed. In this example, on an image of the standard moving picture displayed on the left side of the image display region 41, rectangular target regions ROI1 and ROI2 are doubly designated. An image similar to the image designated in the region of the inner frame ROI1 is subjected to the template matching in a range of the region designated by the outer frame ROI2 and a detected position is displayed in the following image frame. When the region of the moving body following function is set such that the same region is set in the moving image having different cycles and the same phase, a dot-shaped track is obtained as shown in FIG. 17, so that the designated portion can be followed to see how it moves.

(Time Series Image Generating Function)

Figure 18:
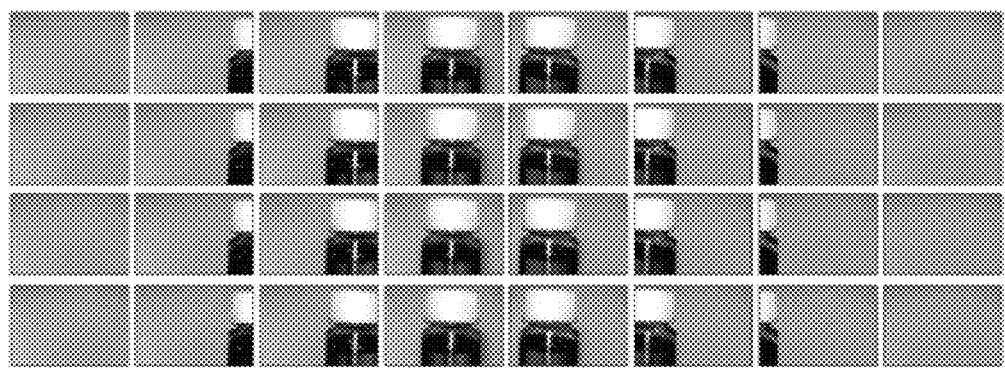
FIG. 18 is an image view showing a behavior to execute a time series image generating function.

Moreover, as still another example of the analyzing function, the moving image observing program has a time series image generating function to display the divided moving images in the different cycles with their phases aligned. FIG. 18 shows a case where the time series image generating function is executed. As shown in this figure, the divided moving images in the different cycles are arranged vertically, and arranged in the form of a matrix so that the phases of the divided moving images are aligned with each other in the vertical direction. Thus, the moving images can be displayed such that they can be divided with respect to each cycle and compared with the phase aligned, so that a different point between the frames can be easily detected.

Figure 19:
FIG. 19 is an image view showing an example displaying only a specific phase of a different divided moving image.

In addition, as shown in FIG. 19, only one specific phase can be displayed other than the case where the plurality of image frames of the divided moving images are displayed. In this example, the image frames of the divided moving image in the one phase are arranged in a lateral direction along the cycles. In this display also, a different point in the cycles can be easily compared at a certain time.

Thus, the continuous moving image is divided with respect to each cycle, and the image frames are displayed in the list with the phases aligned, so that the analyzing operation of the moving images picked up by the high-speed camera which has been conventionally troublesome can be considerably improved in efficiency, and the analyzing operation can be greatly energy-saving and an extremely convenient environment for analysis can be provided.

(Abnormality Monitor Recording Function)

Moreover, after taking the image of the periodic motion of the object, the moving image pickup apparatus can record only an unusual image by evaluating the motion of each cycle. According to this abnormality monitor recording function, the high-speed camera picks up and records the scenes composed of the repeated periodic operations in which products enter and leave the production line of a factory, as the moving image, divides the moving image with respect to each cycle, analyzes it, and records an abnormal one.

For example, in order to analyze an abnormality generation process of the product in the production line, in the case where the high-speed camera picks up the image of the product moving in the production line, it is not known in many cases when an abnormal operation occurs. In this case, the user has to analyze the moving image picked up by the high-speed camera by confirming the enormous amount of data, and searing the image causing the problem from the similar repeated images, which forces the user to bear great burden.

As described above, the moving image pickup apparatus can periodically divide the input moving image using the representative image selected from the moving image as the image trigger, so that the analyzing operation of the moving image by the user can be considerably reduced. However, even in this method, when the vast amount of data has to be processed, the comparing operation becomes also enormous. In addition, when the moving image pickup apparatus is used online, it could fail to pick up a desired scene because a memory source is limited. Thus, the evaluation value is used and only the divided moving image having a high abnormality degree is stored, so that the data amount itself as the analysis target can be reduced, and as only the problematic data is analyzed, the analyzing operation can be effectively performed. In addition, as the process is started from the divided moving image data having the high abnormality degree, the problem can be specified with high probability.

As described above, the picked-up moving image data is divided with respect to each cycle and the motion is evaluated using the moving image for the one cycle. The evaluation value is calculated such that a standard motion pattern which represents a typical motion for the one cycle is previously created by the standard motion pattern obtaining signal 37, and the whole or a part of the standard motion pattern is compared with the whole or a part of the moving image data for the one cycle. The evaluation value is calculated by the degree of the similarity such as a difference or correlation, with the general image.

With the evaluation value, the cycle having a low evaluation value, that is, showing a large difference from the standard motion pattern is regarded as the cycle in which the abnormal operation is generated, and stored in the image memory. At this time, only the cycle which exceeds the certain threshold value is stored in the image memory. Alternatively, the data may be stored as long as an empty image memory exists, and when the empty memory runs out, the data is deleted sequentially from the data having a high evaluation value, that is, showing a small difference from the standard motion pattern, and a new moving image is stored therein. The moving image for one or more cycles before the cycle having the high evaluation value and/or the moving image for one or more cycles after the cycle having the high evaluation value are is recorded together. In addition, while the description has been made of the case where the evaluation value is used when the cycle in which the abnormal operation is generated is specified here, in addition to that, the case where the interval between the standard timing corresponding to each cycle is more than or less than a specified value may be also regarded as the cycle in which the abnormal operation is generated, and stored in the image memory. In this case, as for the order of deleting the data from the image memory after empty memory runs out, it may be set to the lowest, or may be set so as to correspond to the arbitrary evaluation value.

(Phase Alignment)

In comparing to the standard motion pattern, in the case where the phase of the moving image is aligned, the comparison is performed after a start position and an end position of the comparison have been aligned based on the phase information.

(Phase Adjusting Unit)

In addition, when the phase is not aligned among the divided moving images, or the phase is not known, the phase is aligned by a phase adjusting unit. According to the phase adjusting unit, the frame is shifted and a position having a smallest difference is recognized as a position in which the cycle matches, and the evaluation value is calculated at that position. More specifically, while the start position and the end position are shifted by δ frame (δ>0), the comparison is made and the position having the highest evaluation value is regarded as the position in which the phase is aligned, and its evaluation value is set as the evaluation value of the motion.

(Standard Motion Pattern)

The standard motion pattern is previously created by the standard motion pattern obtaining unit 37. The standard motion pattern is the moving image provided by previously recording the standard operation for the one cycle. Alternatively, it may be an average image group provided by recording standard moving image for several cycles, dividing it with respect to each cycle with the phase aligned, and averaging them with respect to each corresponding phase. For example, the moving image for 100 cycles is picked up as a tentative imaging operation, and 5 to 10 kinds of similar patterns are searched to create the standard motion pattern. In addition, as another example, a pattern image group data may be provided such that the moving image for several tens of cycles is picked up and divided with respect to each cycle, and machine learning is performed with respect to each frame of the corresponding phase to compress it to the several kinds of typical pattern images. The pattern image group data can be created by the same technique as the machine learning performed in handwriting recognition.

(Weighting Based on Phase Shift)

Among the image group constituting the one cycle, there is a part having a large variation in each cycle due to a slight shift of the timing, while there is a part having almost no variation among the cycles. Therefore, in the phase having the large variation, an error becomes large and the image becomes abnormal because the phase is largely shifted from that of the standard motion pattern even when its operation is normal originally. In order to prevent the above problem, the whole motion is evaluated such that a degree of variation is calculated in each phase, and provided for the user as the waveform, and the evaluation value is weighted, based on the variation in each phase. In addition, as for the phase whose variation is above a certain value, its motion may not be evaluated.

In addition, as the evaluation value, the above-described reference value which serves as the standard to generate the moving picture waveform may be used.

(Abnormality Monitor Recording Function)

Figure 20:
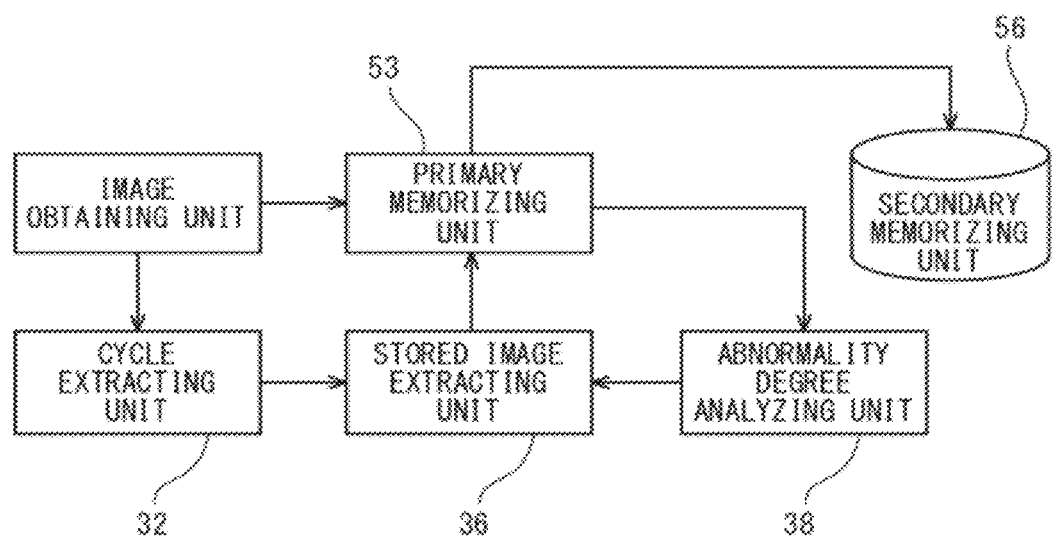
FIG. 20 is a block diagram of a high-speed moving image pickup apparatus to realize an abnormality monitor recording function.

Next, the abnormality monitor recording function will be described in detail with reference to FIG. 20. FIG. 20 is a block diagram of a high-speed imaging apparatus to execute the abnormality monitor recording function. The high-speed imaging apparatus shown in this figure includes the image obtaining unit, the cycle extracting unit 32, the stored image extracting unit 36, an abnormality degree analyzing unit 38, the primary memorizing unit 53, and a secondary memorizing unit 56.

(Abnormality Degree Analyzing Unit 38)

The abnormality degree analyzing unit 38 compares the standard motion pattern for the one cycle representing the previously determined motion serving as the standard of the object, with the input moving image in each cycle to determine an abnormality degree. In addition, the above characteristic amount calculating unit 34 may be composed of the abnormality degree analyzing unit 38, and the abnormality degree may be used as the characteristic amount. Thus, while the characteristic amount is used to divide input moving image with respect to each cycle, it may be used as the abnormality degree, so that the characteristic amount can be used to select the stored moving image.

(Primary Memorizing Unit 53)

The primary memorizing unit 53 is the image memory as described above, and stores the moving image data obtained by the image obtaining unit with respect to each cycle.

(Second Memorizing Unit 56)

The second memorizing unit 56 has memory capacity larger than that of the primary memorizing unit 53, and a hard disk which is low in writing speed is used for it.

(Stored Image Extracting Unit 36)

The stored image extracting unit 36 specifies the moving image in the cycle having the high abnormality degree which is determined by the abnormality degree analyzing unit 38 to be stored in the primary memorizing unit 53. More specifically, a storage queue is created. Thus, the moving image in the cycle having the high importance degree can be surely stored in the secondary memorizing unit 56.

(Storage Queue)

When there is an empty memory in the image memory at the time of recording of the divided moving image, the image is stored therein, and when there is no empty memory, the divided moving image having the low abnormality degree is deleted to create an empty memory block and then the image is stored therein. In addition, when the image is stored in the secondary memorizing unit 56 to save the memory capacity, the storage queue is created to store the image in the decreasing order of the abnormality degree because the storing speed is very slow compared to recording speed.

Referring to FIG. 20, the image obtaining unit obtains the moving image and stores it in the primary memorizing unit 53 and sends it to the cycle extracting unit 32. The image obtaining unit picks up the moving image with the high-speed camera and stores it in the image memory of the primary memorizing unit 53, while it sends the moving image to the cycle extracting unit 32. The cycle extracting unit 32 divides the moving image with respect to each cycle. The cycle extracting unit 32 determines the division point of the cycle based on the moving image or the externally inputted trigger signal, and when it determines the division point, it outputs the signal to the stored image extracting unit 36 to move the storage address to another memory address. Thus, the moving image can be stored, that is, recorded in the different memory address with respect to each cycle.

However, the primary memorizing unit 53 is limited. Therefore, it is necessary to increase empty capacity of the primary memorizing unit 53 by sequentially storing the moving image in the second memorizing unit 56 from the one which has been stored in the primary memorizing unit 53. However, the writing speed of the recording medium such as the hard disk serving as the secondary memorizing unit 56 is one-tenth to one-hundredth of the writing speed of the primary memorizing unit 53 in general, so that the memory runs out during the storage. Therefore, the abnormality degree of each cycle is calculated by the abnormality degree analyzing unit 38 after the storage has been completed, and when there is no empty capacity (available memory) in the primary memorizing unit 53, the moving image is deleted sequentially from the one having the lower abnormality degree in the image memory. Thus, with the lapse of recording time, only the cycle having the high abnormality degree is left in the primary memorizing unit 53.

(Abnormality Degree)

In order to calculate the abnormality degree, the moving image having the normal operation is previously recorded over the several cycles by the tentative imaging operation, and the standard motion pattern is prepared. For example, the image composed of the average image in the same phase in each cycle is set as the normal pattern (standard motion pattern), and the phase of the recorded image in each cycle is matched with that of the normal pattern to find an average value of each frame difference, whereby the abnormality degree can be calculated. In addition, the difference in the cycle divided by the cycle extracting unit 32 can be used as the abnormality degree.

(Setting Procedure of Abnormality Monitor Recording)

Figure 21:
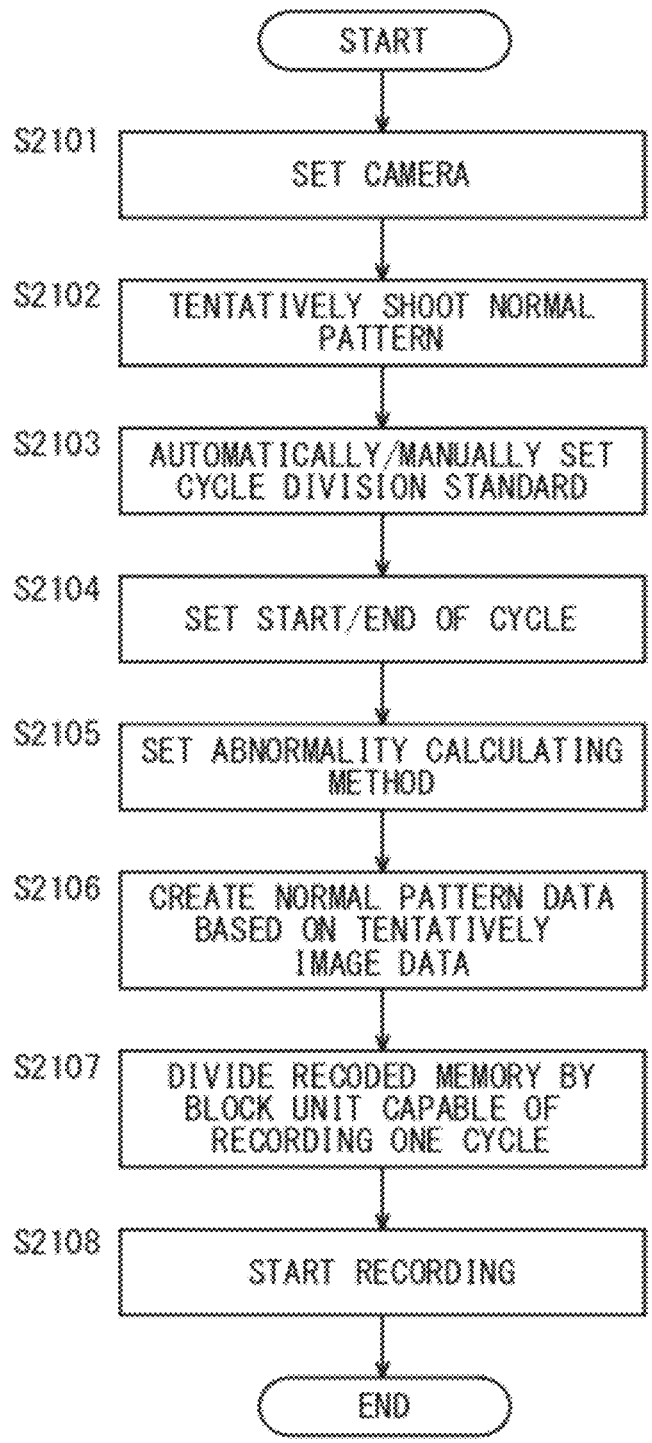
FIG. 21 is a flowchart showing a setting procedure of abnormality monitor recording.

FIG. 21 shows a flowchart of a setting procedure of the abnormality monitor recording. First, in a step S2101, the image obtaining unit is set. Here, the image obtaining unit uses the high-speed camera as the imaging unit 10 to pick up the moving image, and a view and an imaging frame rate of the high-speed camera are set.

Next, in a step S2102, the image of the normal pattern is tentatively picked up. In a step S2103, the standard frame to be divided with respect to each cycle is set. Here, there are two cases where the standard frame is automatically set and it is manually set by the user. When the standard frame is automatically set, the cycle extracting unit 32 sections the input moving image with respect to each cycle, based on the standard timing, as described above.

In addition, when the standard frame is manually set by the user, the user selects the representative image representing one cycle. Based on the selected representative image, the cycle extracting unit 32 selects the image frame which is similar to the representative image, as the standard frame. Alternatively, the user sets the threshold value in the moving picture waveform which will be described later, and the cycle extracting unit 32 divides the moving image with respect to each cycle using a point exceeding the threshold value, as the standard frame.

Then, in a step S2104, the start and end of the cycle are set. For example, the user finely adjusts the cycle automatically set by the cycle extracting unit 32. In a step S2105, the abnormality calculating method is set. Then, in a step S2106, the normal pattern data is created based on the tentative image data. Finally, in a step S2107, the record memory is divided into block units so as to be able to record one cycle. Thus, in a step S2108, the recording is started. As described above, the image of the normal pattern is picked up, the division settings are performed, and the normal pattern data can be created. The normal pattern data can be used in setting the abnormality degree at the time of monitoring and the cycle division.

(Recording Flow During Abnormality Monitor Recording)

Figure 22:
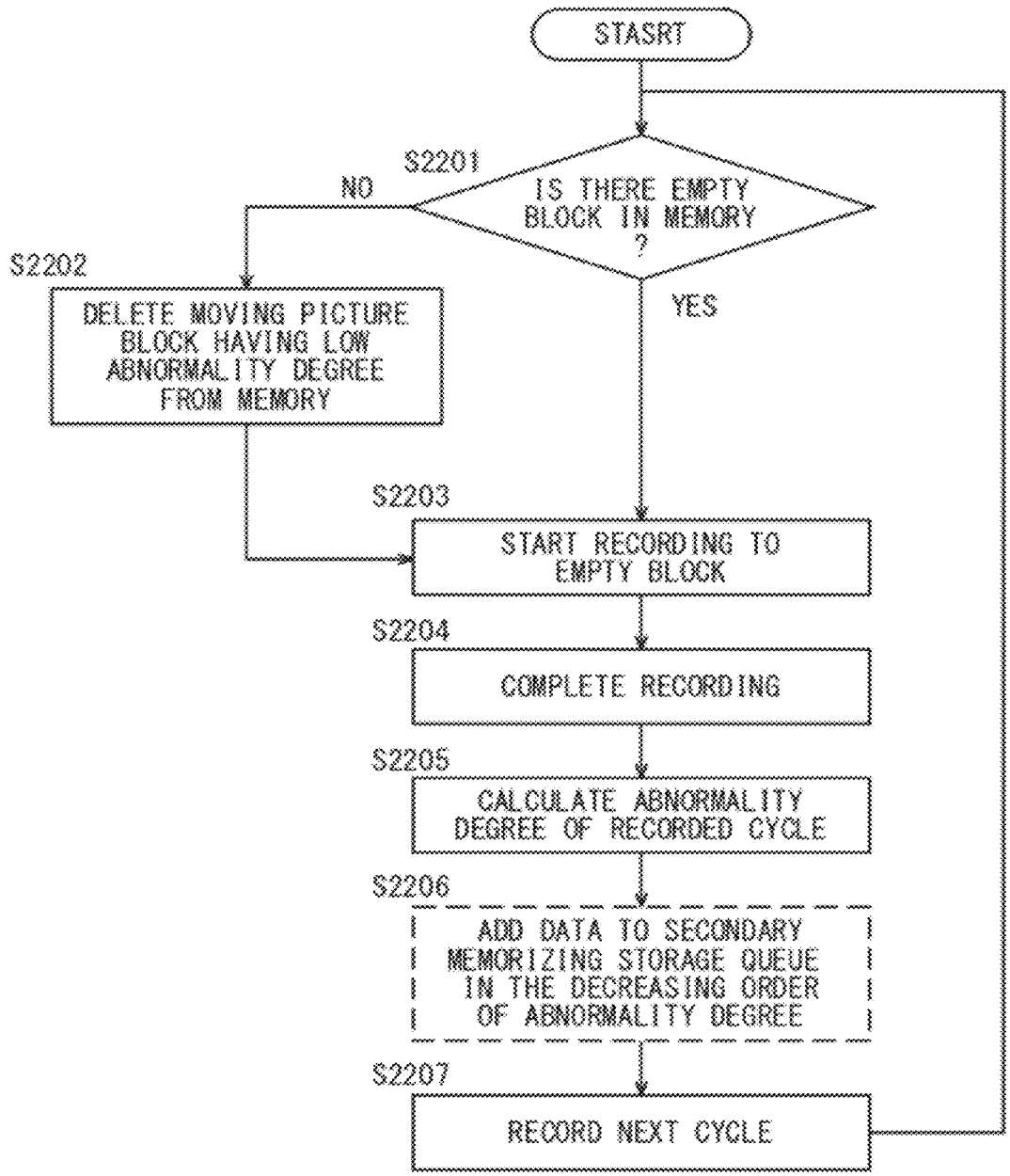
FIG. 22 is a flowchart showing a procedure to execute the abnormality monitor recording function.

The moving image picked up by the high-speed camera is stored, that is, recorded in the image memory serving as the primary memorizing unit 53 with respect to each cycle. At this time, the abnormality degree analyzing unit 38 calculates the abnormality degree of the moving image which is currently recorded, and executes the abnormality monitor recording function to store only the moving image having the high abnormality degree, in the image memory. Hereinafter, the procedure to execute the abnormality monitor recording function for the moving image will be described with reference to a flowchart in FIG. 22.

First, in a step S2201, it is determined whether or not there is an empty block in the image memory. When there is an empty block, the operation proceeds to a step S2203, and when there is no empty block, the moving image block having the low abnormality degree in the image memory is deleted in a step S2202 and the operation proceeds to the step S2203.

Then, in the step S2203, the moving image is stored, that is, recorded in the empty block. Then, in a step S2204, the moving image for the one cycle is recorded, and in a step S2205, the abnormality degree of the recorded cycle is calculated by the abnormality degree analyzing unit 38. Then, in step S2206, the moving image is added to the storage queue to the secondary memorizing unit 56 in the decreasing order of the abnormality degree. Then, in a step S2207, the operation returns to the step S2201 for the next cycle recording, and the above steps are repeated.

The moving image is recorded such that the moving image is divided with respect to each cycle in the above example, but as another example, the frames having the high abnormality degree may be continuously or discretely recorded without regard to the cycle in a case where the abnormality is calculated with respect to each frame.

(Thumbnailing Function; Alarming Function)

In addition, a function may be provided to play back the divided moving image in the cycle having the high abnormality degree which has been recorded in the primary memorizing unit 53, or the secondary memorizing unit 56, in the decreasing order of the abnormality degree, and a thumbnailing function may be provided to display the frame having the highest abnormality degree as a list. In addition, when the abnormality degree exceeds the certain threshold value, an alarm may be outputted or the subsequent recording may be stopped.

INDUSTRIAL APPLICABILITY

The moving image pickup apparatus, the method for observing the moving image, the moving image observing program, and the computer-readable recording medium according to the present invention can be preferably applied to high-speed cameras, high-speed video cameras, image sensors, and image inspecting apparatuses which are used to investigate a cause of abnormality in an FA line, to observe a behavior of a material fracture when a material is fractured at a tensile test of the material, to pick up an image of a high-speed combustion of an internal-combustion engine, to observe a motion behavior in sports, and to continuously pick up an image of a high-speed phenomenon such as collision or discharging in short time.

What is claimed is:

1. A moving image pickup apparatus to pick up a moving image of one or more objects as an imaging target, comprising:
   a high-speed camera configured to obtain an input moving image composed of a plurality of frames, the input moving image including a cyclic scene of the one or more object(s);
   a processor configured to calculate a characteristic amount of each frame or each frame group from the input moving image obtained by the high-speed camera, to automatically select an image from each frame or each frame group of the input moving image obtained by the high-speed camera on the basis of the characteristic amount as a representative image representing a cycle,
   to select
   a standard timing based on the representative image in order to divide the input moving image into each cycle, and to divide
   the input moving image into each cycle on the basis of the standard timing, wherein the processor is configured further to adjust a position of the cycle backward and forward prior to the input moving image being divided into each cycle; and
   a display configured to display the input moving image divided into each cycle on the basis of the standard timing.

2. The moving image pickup apparatus according to claim 1, wherein
   the processor is configured to select an image appearing one time in each cycle, as the representative image.

3. The moving image pickup apparatus according to claim 1, wherein the processor is configured further to calculate a difference by shifting the frame of the divided moving image as a target when the phases of the divided moving images are not known, and regarding a position having a highest evaluation value as a position having an aligned phase.

4. The moving image pickup apparatus according to claim 1,
   wherein the processor is configured further to generate a moving picture waveform on the basis of the characteristic amount calculated,
   the processor is configured to select the standard timing on the basis of the moving picture waveform.

5. The moving image pickup apparatus according to claim 1, further comprising a trigger outputting unit configured to output a trigger signal at a time corresponding to the standard timing.

6. The moving image pickup apparatus according to claim 1, further comprising:
   a primary memory configured to store the respective moving image data in each cycle; and
   wherein the processor is configured to further determine an abnormality degree by comparing a previously determined standard motion pattern for the one cycle representing a standard motion of the object, with the input moving image in each cycle;
   and to specify the moving image in the cycle having a high abnormality degree to be stored in the primary memory.

7. The moving image pickup apparatus according to claim 6, further comprising a secondary memory configured to have large memory capacity and low in writing speed as compared to the primary memory, wherein
   the processor is configured to specify the moving image in the cycle having a high abnormality degree to be kept in the secondary memory, the moving image in the cycle is selected from the respective imaging data in each cycle in the primary memory.

8. The moving image pickup apparatus according to claim 4, wherein
   the displaying unit includes:
   an image display region for displaying the moving image, and
   a waveform display region for displaying the moving picture waveform, and
   when an arbitrary position of the moving picture waveform is selected in the waveform display region, the moving image corresponding to the selected moving picture waveform is displayed in the image display region.

9. The moving image pickup apparatus according to claim 8, wherein
   the processor is configured to change the standard timing under the condition that the moving picture waveform representing the characteristic amount is displayed in the waveform display region, and
   the moving picture waveform displayed in the waveform display region is updated in accordance with changing of the standard timing.

10. The moving image pickup apparatus according to claim 8, wherein
    the processor is configured to change the representative image under the condition that the moving picture waveform showing the characteristic amount is displayed in the waveform display region, and
    the moving picture waveform displayed in the waveform display region is updated in accordance with changing of the standard timing.

11. A method for observing a moving image of one or more objects as an imaging target comprising:
    providing a high-speed camera;
    obtaining an input moving image composed of a plurality of frames, the input moving image including a cyclic scene of one or more object(s) by the high-speed camera;
    calculating a characteristic amount of each frame or each frame group from the input moving image obtained by the high-speed camera;
    adjusting a postion of the cycle back and forward prior to dividing the input moving image into each cycle;
    automatically selecting a first image from each frame or each frame group of the input moving image obtained by the high-speed camera on the basis of the characteristic amount as a representative image representing a cycle;
    selecting a standard timing on the basis of the representative image in order to divide the input moving image into each cycle;
    dividing the input moving image into each cycle on the basis of the standard timing; and
    displaying the input moving image divided into each cycle on the basis of the standard timing.

12. The method according to claim 11, further comprising generating a moving picture waveform on the basis of the characteristic amount calculated, and
    selecting the standard timing on the basis of the moving picture waveform.

13. The method according to claim 11, further comprising:
    storing the respective moving image data in each cycle; and
    determining an abnormality degree by comparing a previously determined standard motion pattern for the one cycle representing a standard motion of the object, with the input moving image in each cycle;

and specifying the moving image in the cycle having a high abnormality degree to be stored.

14. The method according to claim 11, further comprising specifying the moving image in the cycle having a high abnormality degree to be kept in a secondary memory, wherein the moving image in the cycle is selected from the respective imaging data in each cycle for a primary memory.

15. The method according to claim 11, wherein
the displaying includes:
an image display region for displaying the moving image, and
a waveform display region for displaying a moving picture waveform, and
when an arbitrary position of the moving picture waveform is selected in the waveform display region, the moving image corresponding to the selected moving picture waveform is displayed in the image display region.

16. The method according to claim 15, wherein
the standard timing is changeable under the condition that the moving picture waveform representing the characteristic amount is displayed in the waveform display region, and
the moving picture waveform displayed in the waveform display region is updated in accordance with changing of the standard timing.

17. The method according to claim 15, wherein
changing the representative image under the condition that the moving picture waveform showing the characteristic amount is displayed in the waveform display region, and
the moving picture waveform displayed in the waveform display region is updated in accordance with changing of the standard timing.

18. A non-transitory computer-readable recording medium to store or present a moving image observing program to observe a moving image of one or more objects as an imaging target, the program causing a computer to implement the functions of:
obtaining an input moving image composed of a plurality of frames, the input moving image including a cyclic scene of one or more object(s) by a high-speed camera;
calculating a characteristic amount of each frame or each frame group from the input moving image obtained by the high-speed camera;
adjusting a position of the cycle back and forward prior to dividing the input moving image into each cycle;
automatically selecting a first image from each frame or each frame group of the input moving image obtained by the high-speed camera on the basis of the characteristic amount as a representative image representing a cycle;
selecting a standard timing on the basis of the representative image in order to divide the input moving image into each cycle;
dividing the input moving image into each cycle on the basis of the standard timing; and
displaying the input moving image divided into each cycle on the basis of the standard timing.

* * * * *